United States Patent
Kozikowski et al.

(10) Patent No.: US 8,754,132 B2
(45) Date of Patent: Jun. 17, 2014

(54) HIGHLY SELECTIVE 5-HT(2C) RECEPTOR AGONISTS THAT SHOW ANTI-PSYCHOTIC EFFECTS WITH ANTAGONIST ACTIVITY AT THE 5-HT(2B) RECEPTOR

(71) Applicants: The Board of Trustees of the University of Illinois, Urbana, IL (US); The University of North Carolina at Chapel Hill, Chapel Hill, NC (US)

(72) Inventors: Alan Kozikowski, Chicago, IL (US); Bryan Roth, Durham, NC (US); Andreas Svennebring, Nacka (SE); Sung Jin Cho, Daejeon (KR)

(73) Assignees: The Board of Trustees of the University of Illinois, Urbana, IL (US); The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 13/887,996

(22) Filed: May 6, 2013

(65) Prior Publication Data

US 2013/0281539 A1    Oct. 24, 2013

Related U.S. Application Data

(63) Continuation of application No. 13/576,819, filed as application No. PCT/US2011/023535 on Feb. 3, 2011, now Pat. No. 8,492,591.

(60) Provisional application No. 61/301,441, filed on Feb. 4, 2010.

(51) Int. Cl.
   *A01N 33/02*  (2006.01)
(52) U.S. Cl.
   USPC ............ 514/660; 514/659; 514/650; 514/649

(58) Field of Classification Search
   USPC ................... 514/660, 659, 650, 649
   See application file for complete search history.

(56) References Cited

U.S. PATENT DOCUMENTS

| | | | |
|---|---|---|---|
| 6,777,407 B2 | 8/2004 | Sabb et al. |
| 6,953,787 B2 | 10/2005 | Smith et al. |
| 6,962,939 B1 | 11/2005 | Roffey et al. |
| 7,012,089 B2 | 3/2006 | Gao et al. |
| 7,071,185 B2 | 7/2006 | Ramamoorthy et al. |
| 2002/0032199 A1 | 3/2002 | Poss et al. |
| 2005/0020573 A1 | 1/2005 | Smith et al. |
| 2005/0026925 A1 | 2/2005 | Blench et al. |
| 2005/0143452 A1 | 6/2005 | Gross et al. |
| 2005/0197380 A1 | 9/2005 | Roffey et al. |
| 2005/0261347 A1 | 11/2005 | Gross et al. |
| 2009/0105290 A1 | 4/2009 | Sundermann et al. |

FOREIGN PATENT DOCUMENTS

| | | |
|---|---|---|
| WO | WO-00/35922 A1 | 6/2000 |
| WO | WO-01/68653 A1 | 9/2001 |
| WO | WO-02/26747 A1 | 4/2002 |
| WO | WO-2005/007614 A1 | 1/2005 |
| WO | WO-2006/065600 A2 | 6/2006 |
| WO | WO-2006/077025 A2 | 7/2006 |
| WO | WO-2007/000325 A2 | 1/2007 |
| WO | WO-2009/022065 A2 | 2/2009 |

OTHER PUBLICATIONS

International Search Report in international application No. PCT/US2011/023535, dated Oct. 11, 2011.

*Primary Examiner* — Jafar Parsa

(74) *Attorney, Agent, or Firm* — Marshall, Gerstein & Borun LLP

(57) ABSTRACT

Highly selective 5-HT(2C) receptor agonists receptors are disclosed. The 5-HT(2C) receptor agonists are used in the treatments of disease and conditions wherein modulation of 5-HT(2C) receptors provides a benefit, such as obesity and psychiatric disorders.

7 Claims, No Drawings

HIGHLY SELECTIVE 5-HT(2C) RECEPTOR AGONISTS THAT SHOW ANTI-PSYCHOTIC EFFECTS WITH ANTAGONIST ACTIVITY AT THE 5-HT(2B) RECEPTOR

CROSS-REFERENCE TO RELATED APPLICATIONS

This is a continuation of U.S. patent application Ser. No. 13/576,819, filed Dec. 12, 2012, which is the U.S. national phase application of International Application No. PCT/US2011/023535, filed Feb. 3, 2011, which claims the benefit of U.S. provisional patent application No. 61/301,441, filed Feb. 4, 2010, incorporated herein by reference in its entirety.

STATEMENT OF GOVERNMENT INTEREST

This invention was made with government support under grant numbers R01 DA022317, R01 MH61887, N01 MH80032, and U19 MH82441, awarded by NIH/NIDA. The government has certain rights in this invention.

FIELD OF INVENTION

The present invention relates to compounds that modulate 5-HT(2) receptors. More particularly, the present invention relates to highly selective 5-HT(2C) agonists that also may exhibit antagonist activity at the 5-HT(2B) receptor. The compounds are used methods of treating diseases and conditions wherein modulation of 5-HT(2) receptors provide a benefit, such as obesity and psychiatric disorders.

BACKGROUND OF THE INVENTION

5-Hydroxytryptamine (5-HT) mediates or regulates a wide variety of behaviors including, for example, cognition, emotion, attention, and appetite among others. In addition, substantial data indicates that 5-HT is involved in mediating the effects of psychomotor stimulants, such as cocaine and 3,4-methylenedioxy-methamphetamine (MDMA or "ecstasy"). Evidence shows that serotonergic systems in the brain also regulate dopaminergic reward systems and other factors, including the conditioning effects that environmental factors have in maintaining drug taking behavior.

It is understood that the various physiologic effects of 5-HT are based on its interaction with a number of different 5-HT receptor subtypes which activate different intracellular signaling systems. Seven families of 5-HT receptors have been identified, including the 5-HT2 receptor family in which three subtypes are known (5-HT(2A), 5-HT(2B) and 5-HT(2C) receptors). The 5-HT(2) receptor family of serotonin receptors represent key sites of action of serotonin in the brain, and likely comprise the major molecular targets for drugs used in treating a variety of diseases including schizophrenia, depression, anxiety, eating disorders, obsessive-compulsive disorder, chronic pain conditions, and obesity.

The 5-hydroxytryptamine 2C receptor (5-HT(2C)), a prominent central serotonin receptor subtype, is widely distributed throughout the central nervous system (CNS) and is thought to play a role in regulating a wide variety of behavioral processes such as mood, appetite, and sexual behavior (1-4). The 5-HT(2A) receptor mediates the hallucinogenic activity of drugs, such as lysergic acid diethylamide (LSD), and is a major target for treating schizophrenia, insomnia, and other disorders (5). The 5-HT(2B) receptor mediates the potentially lethal valvulopathic side effects of several compounds used as prescription drugs. (6, 7)

5-HT(2C) agonists have demonstrated efficacy in preclinical models of depression, obesity, addiction, and psychosis (8-10). Therapeutics that target the 5-HT(2C) receptor offers a promising means for the treatment of CNS related disorders. However, because the 5-HT(2C) receptor is homologous to the two other family members (11), it is important that 5-HT(2C) agonists developed for clinical use show little if any activity at these subtypes (12). To date, several 5-HT(2C) agonists have shown efficacy in preclinical animal models (13-15), and are currently undergoing human trials (13). In particular, one of the most advanced 5-HT(2C) receptor agonist is Lorcaserin, which is an orally active, antiobesity medication presently in two Phase III trials (16).

Drugs may interact with more than one 5-HT(2) receptor sub-type resulting in potentially undesired side effects. For example, in addition to monoamine transporters, fenfluramine exhibits 5-HT(2C) receptor agonism in vivo, and that the anorectic functions of fenfluramine are due primarily to this latter activity, at least in laboratory animals. It is also clear that 5-HT(2B) receptor agonism is likely responsible for the undesirable cardiopulmonary actions of fenfluramine and related drugs.

These findings indicate that there is a need in the art for drugs that interact selectively with 5-HT(2) receptor sub-types, and, in particular, selective 5-HT(2C) receptor agonists, which exhibit minimal effect on 5-HT(2A) and 5-HT(2B) receptors. Selective 5-HT(2C) receptor agonists can be useful for treatment obesity and related or associated disorders, including hypertension, hyperlipidemia, diabetes, and cardiovascular disease, and avoid interaction with several related and unrelated receptors associated with significant morbidity and mortality, e.g., valvular heart disease associated with activation of the 5-HT(2B) receptor subtype and hallucinations associated with activation of the 5-HT(2A) receptor subtype.

Selective 5-HT(2C) receptor agonists can be useful in the treatment of depression, anxiety, panic disorder, schizophrenia, OCD, epilepsy, and migraine, in addition to obesity. 5-HT(2C) receptor agonists are further disclosed in WO 2006/065600 as useful for treatment of Alzheimer's Disease, in prevention or treatment of senile plaques, and in the treatment of sexual dysfunction in males and females, including the treatment of erectile dysfunction.

A number of synthetic compounds have been reported that show 5-HT(2C) receptor agonistic activity, including in U.S. Pat. Nos. 6,962,939; 6,777,407; 7,012,089; 6,953,787; and 7,071,185; U.S. Patent Publication Nos. 2005/197380; 2005/020573; 2006/154290; 2005/026925; 2005/0143452; 2002/032199; and 2005/0261347; and published PCT applications WO 2000/035922; WO 2006/065600; WO 2006/077025; and WO 2005/007614, for example.

An important advance in the art would be the discovery of selective 5-HT(2C) receptor agonists that are useful in the treatment of diseases and conditions wherein 5-HT(2C) receptor agonism provides a benefit, such as psychiatric disorders, addictive behaviors, cognition disorders, obesity, movement disorders, and compound addiction, for example. A significant need exists in the art for efficacious compounds, compositions, and methods useful in the treatment of such diseases and conditions, alone or in conjunction with other therapies used to treat these diseases and conditions. The present invention is directed to meeting this need.

SUMMARY OF THE INVENTION

The present invention relates to 5-HT(2C) receptor agonists, pharmaceutical compositions comprising the 5-HT(2C)

receptor agonists, and methods of treating diseases and conditions wherein agonism of 5-HT(2C) receptors provides a benefit, such as psychiatric disorders and obesity, comprising administering a therapeutically effective amount of a 5-HT(2C) receptor agonist to an individual in need thereof. The present 5-HT(2C) receptor agonists exhibit selectivity over other members of the 5-HT(2) family of receptors.

More particularly, the present invention relates to 5-HT(2C) agonists having a structural formula (I):

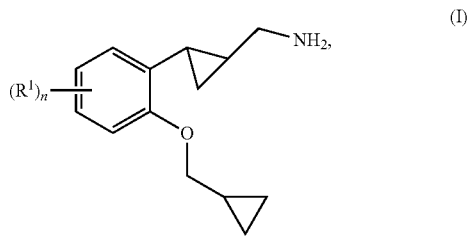

wherein $R^1$, independently, is selected from the group consisting of $C_{1-6}$alkyl, hydroxy$C_{1-6}$alkyl, halo$C_{1-6}$alkyl, $C_{1-6}$alkenyl, —$CF_3$, —$OCF_3$, $C_{1-6}$heteroalkyl, —$OR^a$, —$SR^a$, halo, —$NO_2$, —CN, —NC, —C(=O)$R^a$, —C(=C)$OR^a$, —N($R^a$)($R^b$), —C(=O)N($R^a$)($R^b$), —$SO_2$N($R^a$)($R^b$), —$NR^cC$(=O)$R^a$, —N=C($R^a$)($R^b$), —$NR^cC$(=O)$OR^a$, —$SO_2R^a$, —$SO_3R^a$, —P(O)(O$R^a$), —P(=O)(O$R^a$)(O$R^b$), and —NH—P(=O)(O$R^a$)(O$R^b$);

$R^a$ and $R^b$, independently, are selected from the group consisting of H, $C_{1-6}$alkyl, aryl, heteroaryl, cycloalkyl, and heterocycloalkyl;

$R^c$ is H or $C_{1-6}$alkyl;

and n is an integer 0, 1, 2, 3, or 4;

or a pharmaceutically acceptable salt or hydrate thereof.

The present compounds modulate receptors of the 5-HT(2) family of receptors, and particularly 5-HT(2C) receptors. In some embodiments, the present compounds selectively modulate the 5-HT(2C) receptor, while exhibiting significantly less or no activity on the 5-HT(2B) receptor. In some embodiments, the present compounds selectively modulate the 5-HT(2C) receptor, while exhibiting significantly less or no activity on the 5-HT(2A) receptor. In some embodiments, the present compounds are agonists for the 5-HT(2C) receptor. In preferred embodiments, compounds of this invention are selective agonists for the 5-HT(2C) receptor, while exhibiting significantly less or no agonist activity on the 5-HT(2A) receptor and/or the 5-HT(2B) receptor.

In another embodiment, the present invention provides a method of treating a condition or disease by administering a therapeutically effective amount of a 5-HT(2C) receptor agonist of structural formula (I) to an individual in need thereof. The disease or condition of interest is treatable by modulating the activity of 5-HT(2C) receptors, for example, psychiatric disorders, addictive behaviors, cognitive disorders, obesity, movement disorders, and compound addictions.

Another embodiment of the present invention provides a method of treating a disease or condition by modulating 5-HT(2C) receptor activity comprising administering to an individual in need thereof, such as a human, a therapeutically effective amount of a compound of structural formula (I). The compound of structural formula (I) can be administered as the sole therapy, or in conjunction with a therapeutically effective amount of a second therapeutic agent useful in a treatment of the disease or condition.

In another embodiment, the present invention provides a pharmaceutical composition comprising a compound of structural formula (I) and a pharmaceutically acceptable excipient.

Another embodiment of the present invention is to utilize a compound of structural formula (I) and an optional second therapeutically active agent in a method of treating an individual for a disease or condition wherein modulation of 5-HT(2C) receptor activity provides a benefit.

In a further embodiment, the invention provides for use of a composition comprising a compound of structural formula (I) and an optional second therapeutic agent for the manufacture of a medicament for treating a disease or condition of interest, e.g., a psychiatric disorder.

Still another embodiment of the present invention is to provide a kit for human pharmaceutical use comprising (a) a container, (b1) a packaged composition comprising a compound of structural formula (I), and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition of interest.

The compound of structural formula (I) and the second therapeutic agent can be administered together as a single-unit dose or separately as multi-unit doses, wherein the compound of structural formula (I) is administered before the second therapeutic agent, or vice versa. It is envisioned that one or more dose of a compound of structural formula (I) and/or one or more dose of a second therapeutic agent can be administered.

In one embodiment, a compound of structural formula (I) and a second therapeutic agent are administered simultaneously. In related embodiments, a compound of structural formula (I) and a second therapeutic agent are administered from a single composition or from separate compositions. In a further embodiment, a compound of structural formula (I) and a second therapeutic agent are administered sequentially. A compound of structural formula (I) can be administered in an amount of about 0.005 to about 500 milligrams per dose, about 0.05 to about 250 milligrams per dose, or about 0.5 to about 100 milligrams per dose.

An additional embodiment of the present invention is a method for modulating a 5-HT(2C) receptor in vivo or in vitro comprising contacting the receptor with one or more compound of structural formula (I). In specific embodiments, the method stimulates or activates the 5-HT(2C) receptor. In specific embodiments, the compounds of structural formula (I) are 5-HT(2C) receptor agonists or selective agonists.

These and other novel aspects of the present invention will become apparent from the following detailed description of the preferred embodiments.

DETAILED DESCRIPTION OF THE PREFERRED EMBODIMENTS

The present invention is directed to novel modulators of 5-HT(2C) activity and their use in therapeutic treatments of, for example, psychiatric disorders, obesity, cognitive disorders, addiction, movement disorders, and compound addiction. In some embodiments, the present compounds selectively modulate 5-HT(2C) receptors over other 5-HT(2) receptors.

The present invention is described in connection with preferred embodiments. However, it should be appreciated that the invention is not limited to the disclosed embodiments. It is understood that, given the description of the embodiments of the invention herein, various modifications can be made by a person skilled in the art.

The term "a disease or condition wherein modulation of 5-HT(2C) receptors provides a benefit" pertains to a condition in which 5-HT(2C) receptors and/or the action of 5-HT(2C) receptors is important or necessary, e.g., for the onset, progress, expression of that disease or condition, or a disease or a condition which is known to be treated by a modulation of 5-HT(2C) receptors. Examples of such conditions include, but are not limited to, schizoaffective disorders, schizophrenia, clinical depression, bipolar disorder, addictive behaviors, compound addiction (e.g., cocaine, metamphetamine, and amphetamine), obsessive compulsive disorder, movement disorders (e.g., Huntington's disease, Parkinson's disease, and dyskinesia); cognition disorders (e.g., Alzheimer's disease and mild cognitive impairment), metabolic disorders (e.g., dyslipidemia, Type 2 diabetes, metabolic syndrome, and obesity), and eating disorders. One of ordinary skill in the art is readily available to determine whether a compound treats a disease or condition mediated by 5-HT(2C) receptors for any particular cell type, for example, by assays which conveniently can be used to assess the activity of particular compounds.

The term "second therapeutic agent" refers to a therapeutic agent different from a compound of structural formula (I) and that is known to treat the disease or condition of interest. For example when obesity is the disease or condition of interest, the second therapeutic agent can be a known anti-obesity drug.

As used herein, the terms "treat," "treating," "treatment," and the like refer to eliminating, reducing, relieving, reversing, and/or ameliorating a disease or condition and/or symptoms associated therewith. Although not precluded, treating a disease or condition does not require that the disease, condition, or symptoms associated therewith be completely eliminated, including the treatment of acute or chronic signs, symptoms and/or malfunctions. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition, "treatment" therefore also includes relapse prophylaxis or phase prophylaxis. The term "treat" and synonyms contemplate administering a therapeutically effective amount of a compound of the invention to an individual in need of such treatment. A treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that, when administered, is (are) sufficient, to efficaciously deliver the active ingredient(s) for the treatment of condition or disease of interest to an individual in need thereof.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a compound of structural formula (I) can be administered at the same time or sequentially in any order at different points in time as a second therapeutic agent. A present compound and the second therapeutic agent can be administered separately, in any appropriate form and by any suitable route. When a present compound and the second therapeutic agent are not administered concurrently, it is understood that they can be administered in any order to a subject in need thereof. For example, a present compound can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment, to an individual in need thereof. In various embodiments, a compound of structural formula (I) and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The term "agonist" refers generally to a compound that interacts with and activates a receptor, such as one or more of the receptors of the 5-HT2 family of receptors, and initiates a physiological or pharmacological response characteristic of that receptor.

The term "antagonist" refers generally to a compound that binds to the receptor at the same site as an agonist, but which does not activate the intracellular response initiated by the active form of the receptor, and as such an antagonist can inhibit the intracellular responses by agonists.

As used herein the term "selective 5-HT(2C) receptor agonist" means an agonist compound that is selective for binding and activation of 5-HT(2C) receptors compared to the other receptors of the 5-HT2 family of receptors. An agonist of this invention can be selective for the 5-HT(2C) receptor over the 5-HT(2B) receptor, be selective for the 5-HT(2C) receptor over the 5-HT(2A) receptor, or be selective for the 5-HT(2C) receptor over both the 5-HT(2B) and 5-HT(2A) receptors. In some embodiments, a present 5-HT(2C) receptor agonist can exhibit agonist activity with respect to the 5-HT(2A) receptor. A selective 5-HT(2C) receptor agonist can exhibit a 5-fold, 10-fold, 20-fold, 30-fold, 40-fold, 50-fold, 60-fold, 70-fold, 80-fold, 90-fold, 100-fold, or 200-fold or more higher activity for the 5-HT(2C) receptor compared to either or both of the 5-HT(2B) or 5-HT(2A) receptors.

Selectivity can be assessed, for example, by determining $EC_{50}$ ratios for different receptors. Any method known in the art to be reliable and accurate for measuring receptor agonist activity can be used to assess selectivity of a given agonist. As understood by one skilled in the art, selectivity can be determined, for example, using a receptor binding assay or a functional assay. In specific embodiments, methods described in the examples herein or in references cited herein can be employed. In specific embodiments herein, 5-HT(2C) receptor agonists of this invention can also exhibit selectively over receptors of 5-HT families other than those of the 5-HT2 family. In specific embodiments herein, 5-HT(2C) receptor agonists of this invention may exhibit antagonist activity for 5-HT(2B) receptors.

In some embodiments, a present 5-HT(2C) receptor agonist exhibits an $EC_{50}$ value for activation of human 5-HT(2C) receptors of 100 nM or less. In preferred embodiments, the 5-HT(2C) receptor agonists exhibit $EC_{50}$ values for activation of human 5-HT(2C) receptors of 25 nM or less. In more preferred embodiments, 5-HT(2C) receptor agonists exhibit $EC_{50}$ values for activation of human 5-HT(2C) receptors of 10 nM or less. In some embodiments, compounds of the present invention exhibit 5-fold or more selectivity as agonists for 5-HT(2C) receptors compared to 5-HT(2B) receptors or 5-HT(2A) receptors as assessed by determination of $EC_{50}$ ratios. In some embodiments, compounds of present invention exhibit 10-fold or more selectivity as agonists for 5-HT(2C) receptors compared to 5-HT(2B) receptors or 5-HT(2A) receptors, as assessed by determination of $EC_{50}$ ratios. In preferred embodiments, the present compounds exhibit 100-fold or more selectivity as agonists for 5-HT(2C) receptors compared to 5-HT(2B) receptors or 5-HT(2A) receptors, as assessed by determination of $EC_{50}$ ratios.

The use of the terms "a", "an", "the", and similar referents in the context of describing the invention (especially in the context of the claims) are to be construed to cover both the singular and the plural, unless otherwise indicated. Recitation of ranges of values herein merely serve as a shorthand method of referring individually to each separate value falling within the range, unless otherwise indicated herein, and each separate value and subrange is incorporated into the specification as if it were individually recited herein. The use of any and all examples, or exemplary language (e.g., "such as" and "like") provided herein, is intended to better illustrate the invention and is not a limitation on the scope of the invention unless otherwise claimed. No language in the specification should be construed as indicating any non-claimed element as essential to the practice of the invention.

Selective 5-HT(2C) receptor agonists are known. For example, the following compound 1 is a potent, moderately selective 5-HT(2C) agonist having a 120- and 14-fold selectivity over 5-HT(2A) and 5-HT(2B), respectively ($EC_{50}$=585, 65, and 4.8 nM at the 2A, 2B, and 2C subtypes, respectively). Compound 1 (10-60 mg/kg) also demonstrated moderate antidepressant-like effects in a commonly used behavioral assay (15).

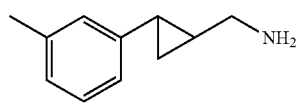

1

However, compound 1 does not exhibit sufficient selectivity over the 5-HT(2B) receptor to qualify as a potential clinical candidate. In particular, the degree of selectivity was considered too low to avoid side effects attributed to 5-HT(2B) activity. Accordingly, new drug candidates with an increased subtype selectivity including dual 5-HT(2B) receptor antagonism/5-HT(2C) receptor agonism were sought.

The present invention is directed to 5-HT(2C) receptor agonists of structural formula (I), compositions comprising a compound of structural formula (I), and therapeutic uses of compounds of structural formula (I):

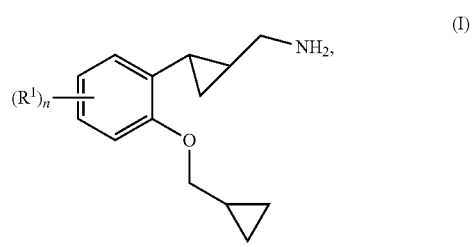

(I)

wherein $R^1$, independently, is selected from the group consisting of $C_{1-6}$alkyl, hydroxy$C_{1-6}$alkyl, halo$C_{1-6}$alkyl, $C_{1-6}$alkenyl, —$CF_3$, —$OCF_3$, $C_{1-6}$heteroalkyl, —$OR^a$, —$SR^a$, halo, —$NO_2$, —CN, —NC, —C(=O)$R^a$, —C(=C)$OR^a$, —N($R^a$)($R^b$), —C(=O)N($R^a$)($R^b$), —$SO_2$N($R^a$)($R^b$), —$NR^cC$(=O)$R^a$, —N=C($R^a$)($R^b$), —$NR^cC$(=O)$OR^a$, —$SO_2R^a$, —$SO_3R^a$, —P(O)($OR^a$), —P(=O)($OR^a$)($OR^b$), and —NH—P(=O)($OR^a$)($OR^b$);

$R^a$ and $R^b$, independently, are selected from the group consisting of H, $C_{1-6}$alkyl, aryl, heteroaryl, cycloalkyl, and heterocycloalkyl;

$R^c$ is H or $C_{1-6}$alkyl;

and n is an integer 0, 1, 2, 3, or 4;

or a pharmaceutically acceptable salt or hydrate thereof.

In some preferred embodiments, $R^1$ is selected from the group consisting of halo, $OR^a$, $SR^a$, $NO_2$, CN, NC, $C_{1-6}$alkyl, halo$C_{1-6}$alkyl, $OCF_3$, $C_{1-6}$heteroalkyl, and hydroxy$C_{1-6}$alkyl. In more preferred embodiments, $R^1$ is selected from the group consisting of fluoro, chloro, bromo, OH, $OCH_3$, $OCF_3$, $CF_3$, and $NO_2$. In preferred embodiments, n is 0, 1, or 2.

The compounds of structural formula (I) modulate 5-HT(2C) receptors and are useful in the treatment of a variety of diseases and conditions. In particular, compounds of structural formula (I) are used in methods of treating a disease or condition wherein activity of 5-HT(2C) receptors provides a benefit, for example, psychiatric conditions and obesity. The methods comprise administering a therapeutically effective amount of a compound of structural formula (I) to an individual in need thereof.

The present methods also encompass administering a second therapeutic agent to the individual in addition to a compound of structural formula (I). The second therapeutic agent is selected from agents, such as drugs and adjuvants, known as useful in treating the disease or condition afflicting the individual, e.g., a therapeutic agent known as useful in treating a particular psychiatric disorder.

As used herein, the term "alkyl" refers to straight chained and branched saturated hydrocarbon groups, nonlimiting examples of which include methyl, ethyl, and straight chain and branched propyl, butyl, pentyl, and hexyl groups containing the indicated number of carbon atoms. The term $C_n$ means the alkyl group has "n" carbon atoms.

The term "alkylene" refers to a bidentate moiety obtained by removing two hydrogen atoms from an alkane. An "alkylene" is positioned between two other chemical groups and serves to connect them. An example of an alkylene group is —(CH$_2$)$_n$—. An alkyl, e.g., methyl, or alkylene, e.g., —CH$_2$CH$_2$—, group can be substituted, independently, with one or more of halo, trifluoromethyl, trifluoromethoxy, hydroxy, alkoxy, nitro, cyano, alkylamino, and amino groups, for example.

The term "alkenyl" is defined identically as "alkyl," except for containing a carbon-carbon double bond, e.g., ethenyl, propenyl, and butenyl. The term "alkenylene" is defined identically to "alkylene" except for containing a carbon-carbon double bond.

The term "heteroalkyl" refers to an alkyl group having one or more, and typically one to three, heteroatoms in the carbon chain of the alkyl group. The heteroatoms, independently, are selected from O, S, and NR, wherein R is hydrogen, alkyl, cycloalkyl, heterocycloalkyl, aryl, and heteroaryl. A term such as "C$_{1-6}$heteroalkyl" means that the group contains 1 to 6 carbon atoms in addition to the heteroatoms.

The term "perfluoroalkyl" is defined as an alkyl group wherein all hydrogen atoms are replaced by fluorine atoms.

The term "halo" is defined as fluoro, chloro, bromo, and iodo.

The term "hydroxy" is defined as —OH.

The term "alkoxy" is defined as —OR, wherein R is alkyl. The term "perfluoroalkoxy" is defined as an alkoxy group wherein all hydrogen atoms are replaced by fluorine atoms.

The term "amino" is defined as —NR$_2$, wherein each R group, independently, is hydrogen, alkyl, cycloalkyl, heterocycloalkyl, heteroaryl, or aryl, or both R groups are taken together with the N to which they are attached to form a 3 to 8 membered ring.

The term "nitro" is defined as —NO$_2$.
The term "cyano" is defined as —CN.
The term "trifluoromethyl" is defined as —CF$_3$.
The term "trifluoromethoxy" is defined as —OCF$_3$.
As used herein, compounds such as

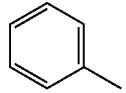

is an abbreviation for

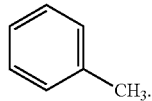

In addition, compounds such as

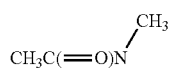

is an abbreviation for

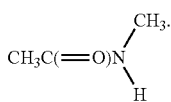

As used herein, the term "aryl" refers to a monocyclic aromatic group, e.g., phenyl. Unless otherwise indicated, an aryl group can be unsubstituted or substituted with one or more, and in particular one to five, groups independently selected from, for example, halo, alkyl, alkenyl, —OCF$_3$, —NO$_2$, —CN, —NC, —OH, alkoxy, amino, alkylamino, —CO$_2$H, —CO$_2$alkyl, alkynyl, cycloalkyl, nitro, sulfhydryl, imino, amido, phosphonate, phosphinate, silyl, alkylthio, sulfonyl, sulfonamide, aldehyde, heterocycloalkyl, trifluoromethyl, aryl, and heteroaryl. Exemplary aryl groups include, but are not limited to, phenyl, fluorophenyl, methylphenyl, methoxyphenyl, trifluoromethylphenyl, nitrophenyl, 2,4-methoxychlorophenyl, and the like.

As used herein, the term "heteroaryl" refers to a monocyclic ring system containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, —OCF$_3$, —NO$_2$, —CN, —NC, —OH, alkoxy, amino, alkylamino, —CO$_2$H, —CO$_2$alkyl, alkynyl, cycloalkyl, nitro, sulfhydryl, imino, amido, phosphonate, phosphinate, silyl, alkylthio, sulfonyl, sulfonamide, aldehyde, heterocycloalkyl, trifluoromethyl, aryl, and heteroaryl. Examples of heteroaryl groups include, but are not limited to, thienyl, furyl, oxazolyl, thiophenyl, triazolyl, isothiazolyl, isoxazolyl, imidazolyl, pyrimidinyl, thiazolyl, thiadiazolyl, pyridinyl, pyridazinyl, pyrazolyl, pyrazinyl, tetrazolyl, oxazolyl, pyrrolyl, and triazinyl.

As used herein, the term "C$_{3-8}$cycloalkyl" means a monocyclic aliphatic ring containing three to eight carbon atoms, either saturated or unsaturated.

As used herein, the term "heterocycloalkyl" means a monocyclic or a bicyclic aliphatic ring containing 3 to 10 total atoms, either saturated or unsaturated, of which one to five of the atoms are independently selected from nitrogen, oxygen, and sulfur and the remaining atoms are carbon.

The term "haloalkyl" refers to an alkyl group as defined herein substituted by one or more halides (i.e., F—, Cl—, I—, and/or Br—) as defined herein, which may be the same or different.

The term "hydroxyalkyl" refers to an alkyl group substituted by one or more hydroxyl groups. An exemplary hydroxyalkyl group is hydroxymethyl (—CH$_2$—OH).

Alkyl, alkenyl, cycloalkyl, heterocycloalkyl, aryl, and heteroaryl groups may be substituted or unsubstituted. These groups may be optionally substituted as described herein and may contain non-hydrogen substituents dependent upon the number of carbon or other atoms in the group and the degree of unsaturation of the group.

All groups defined herein therefore can be optionally substituted. Optional substitution refers to substitution with one or more of the following functional groups: nitro, azido, cyano, isocyano, halogen (Cl, F, Br, or I), hydroxyl, alkyl (including C$_{1-6}$ alkyl), alkenyl, alkynyl, aryl, heteroaryl, arylalkyl, heteroarylalkyl, heterocyclyl, acyl, formyl, acetyl, haloalkyl, haloary, alkyloxy (including C$_{1-6}$ alkoxy), alkenoxy, alkynoxy, aryloxy, benzyloxy, phenyloxy (benzoyl), acyloxy, alkyl acyloxy, oxycarbonyl, alkyl oxycarbonyl —NH$_2$ (or —NH$_{3+}$), amino, alkylamino, arylamino, amido, alkyl amido, arylamido, —CO—NH$_2$, imino, alkylimino, arylimino, ether, thioether, —SH, sulfenyl, alkyl sulfenyl (including C$_{1-6}$ alkyl sulfenyl and C1-C3 alkyl sulfenyl), hydroxyalkyl, haloalkyl, fluoroalkyl, pefluoroalkyl, trifluoromethyl, sulfonate, sulfonyl, phosphonate, phosphinate, or silyl, wherein alkyl, alkenyl, alkynyl, aryl, heteroaryl, arylalkyl, heteroarylalkyl, and heterocycloalkyl groups of the substituents are in turn optionally substituted with one or more of: nitro, azido, cyano, isocyano, halogen, —NH$_2$ (or —NH$_3^+$), hydroxyl, —CO—NH$_2$, —COOH (or carboxylate), or —SH.

Additionally, salts and hydrates of the present 5-HT(2C) receptor agonists also are included in the present invention and can be used in the methods disclosed herein. The present invention further includes all possible stereoisomers and geometric isomers of the compounds of structural formula (I). The present invention includes both racemic compounds and optically active isomers. When a compound of structural formula (I) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the compounds of structural formula (I) are possible, the present invention is intended to include all tautomeric forms of the compounds.

Compounds of the invention can exist as salts. Pharmaceutically acceptable salts of the present 5-HT(2C) receptor agonists often are preferred in the methods of the invention. As used herein, the term "pharmaceutically acceptable salts" refers to salts or zwitterionic forms of the compounds of structural formula (I). Salts of compounds of formula (I) can be prepared during the final isolation and purification of the compounds or separately by reacting the compound with an acid having a suitable cation. The pharmaceutically acceptable salts of compounds of structural formula (I) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, tartaric, and citric. Nonlimiting examples of salts of compounds of the invention include, but are not limited to, the hydrochloride, hydrobromide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and stearyl chlorides, bromides, and iodides; and benzyl and phenethyl bromides. In light of the foregoing, any reference to compounds of the present invention appearing herein is intended to include compounds of structural formula (I) as well as pharmaceutically acceptable salts, hydrates, or prodrugs thereof.

The compounds of structural formula (I) may contain one or more asymmetric carbon atoms, such that the compounds can exist in different stereoisomeric forms. The compounds can be, for example, racemates or optically active forms. The present invention therefore encompasses racemic forms of the compounds of structural formula (I), as well as the individual enantiomers and non-racemic mixtures thereof. The optically active forms can be obtained by resolution of the racemates or by asymmetric synthesis. In some preferred embodiments of the invention, enantiomers of the invention exhibit specific rotation [α] that is +(positive). Preferably, the (+) enantiomers are substantially free of the corresponding (−) enantiomer. Thus, an enantiomer substantially free of the corresponding enantiomer refers to a compound which is isolated or separated via separation techniques or is prepared free of the corresponding enantiomer. "Substantially free" means that the compound is made up of a significantly greater proportion of one enantiomer. In preferred embodiments the compound is made up of at least about 90% by weight of a preferred enantiomer. In other embodiments of the invention, the compound is made up of at least about 99% by weight of a preferred enantiomer. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., "Enantiomers, Racemates and Resolutions" (Wiley Interscience, New York, 1981); Wilen, S. H., et al., *Tetrahedron* 33:2725 (1977); Eliel, E. L. "Stereochemistry of Carbon Compounds" (McGraw-Hill, N.Y., 1962); Wilen, S. H. "Tables of Resolving Agents and Optical Resolutions" p. 268 (E. L. Eliel, Ed., Univ. of Notre Dame Press, Notre Dame, Ind. 1972).

Synthetic Methods

Compounds of the present invention are prepared employing methods as described herein or are prepared by routine modification or adaptation of the methods herein, for example, by selection of starting materials, or variation of reagents, solvents, and/or purification methods, in view of knowledge in the art.

Compounds of the present invention were prepared using the following synthetic schemes for compounds 12 and 18. Additional compounds can be prepared by proper selection of starting materials. In particular, the 2-cyclopropylmethyloxy-5-fluoro substituted derivative 12 was synthesized according to the steps shown in Scheme 1. The starting compound 9 was prepared by employing the standard sequence of reactions as previously reported (15). The amino group of the phenolic derivative 9 was protected using Boc-anhydride. The N-Boc protected derivative 10 then was alkylated with cyclopropylmethyl bromide followed by subsequent deprotection to provide the racemic compound 12.

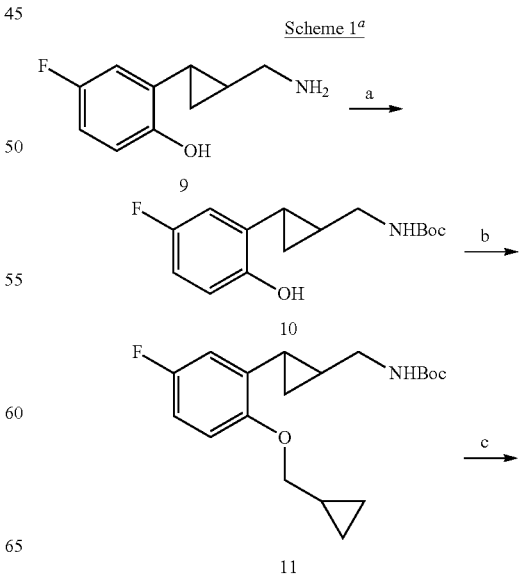

Scheme 1$^a$

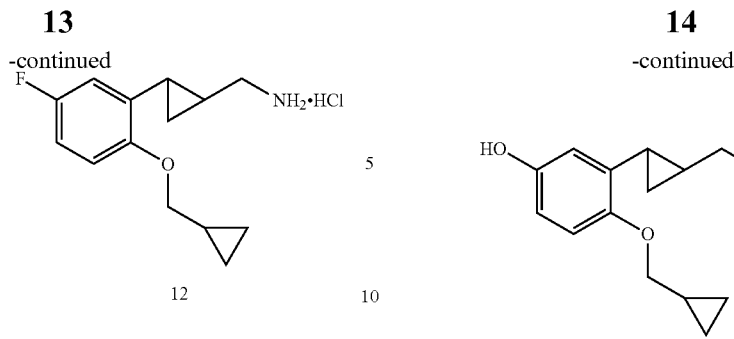

*Reagents and conditions:
a Boc₂O, triethylamine, CH₂Cl₂, 0° C. to rt, 5 h.
b (bromomethyl)cyclopropane, K₂CO₃, DMF, 60° C., 20 h.
c 2M HCl, rt, 48 h.

To synthesize the 2-cyclopropylmethyloxy-5-hydroxy substituted derivative 18, the 2-cyclopropylmethyloxy intermediate 16 was prepared through a sequence of selective protection and alkylation steps (17). Next, the pivaloyl and Boc protecting groups were removed sequentially to afford the final product 18 (Scheme 2).

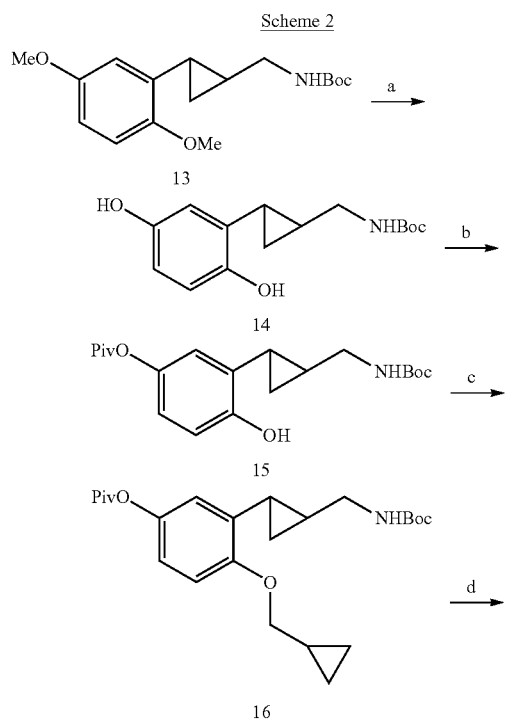

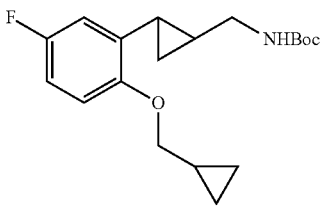

*Reagents and conditions:
a (i) BBr₃, CH₂Cl₂, -78° C. to rt, 6 h; (ii) Boc₂O, triethylamine, CH₂Cl₂, 0° C. to rt, 1 h.
b Piv—Cl, CH₂Cl₂, triethylamine, 0° C. to rt, 6 h.
c (bromomethyl)cyclopropane, K₂CO₃, DMF, 60° C., 20 h.
d NaOtBu, MeOH, rt, 1 h.
e 2M HCl, rt, 48 h.

To prepare the optically pure enantiomers of compound 12 (Scheme 3), a chiral separation of the N-Boc protected fluoro derivative 11 using Chiralpack AD column was performed. Under isocratic conditions (7% isopropanol in hexane), the individual enantiomers were conveniently separated in pure (>99%) state. Due to the high resolution, stacked injections could be employed in order to increase throughput. The chiral separation was performed on intermediate 11 because of the ease of the separation and the ready cleavage of the resulting enantiomers under acidic conditions.

The resulting enantiomers (+)-11 and (−)-11 were then converted individually to (−)- and (+)-trans-[2-(2-cyclopropylmethyloxy-5-fluorophenyl)cyclopropyl]-methylamine hydrochloride ((−)-12 and (+)-12), respectively, using the same method as described above for the racemate. For preparation of the pure enantiomers of compound 18, intermediate 17 was used for the chiral separation.

Scheme 3*

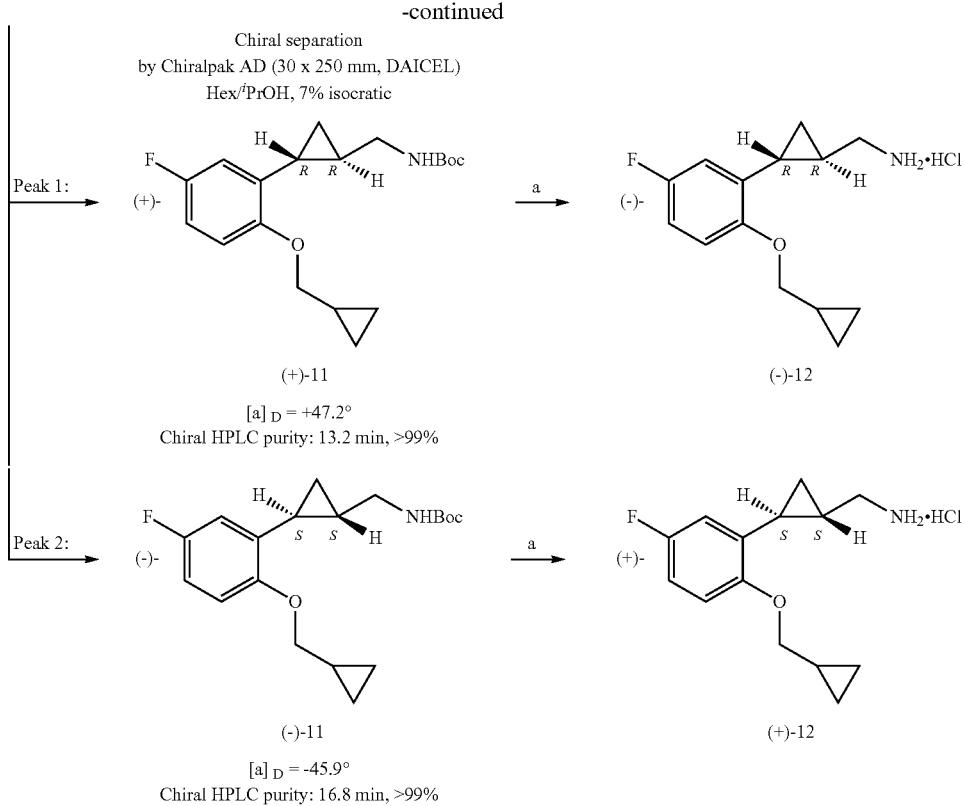

*Reagents and conditions:
a 2M HCl, rt, 48 h.

The detailed preparation of compounds 12 and 18 is as follows:

General. $^1$H and $^{13}$C NMR spectra were obtained with a Bruker Avance spectrometer at 400 and 100 MHz, respectively. $^1$H chemical shifts (δ) were reported in ppm downfield from internal Me$_4$Si. Mass spectra were measured in positive mode electrospray ionization (ESI). Optical rotations were measured with an AUTOPOL IV (Rudolph Research Analytical) instrument. TLC was performed on silica gel 60F 254 glass plates. Column chromatography was performed using CombiFlash® Rf system with RediSep® Rf or alternatively using Merck silica gel (230-400 mesh). Analytical HPLC was performed using an Agilent 1100 with a Variable wavelength detector G1314A system equipped with the Phenomenex Luna C 18 column (4.6×150 mm; 5 μm). Method: H$_2$O/MeCN or MeOH (0.1% TFA), 90/10→0/100 in 18 min, +2 min isocratic, flow rate of 1.6 mL/min, λ=280 nm. The purity of the target compounds was determined to be >98% by analytical HPLC. Chiral HPLC was performed using a Shimadzu LC8A HPLC system with UV-Vis. SPD-10avp detector system equipped with Chiralpak AD (10.0×250 mm, DAICEL) and Chiralpak AD (30.0×250 mm, DAICEL) columns used for chiral HPLC analysis and separation, respectively. Starting materials were obtained from Aldrich, Alfa Aesar, or Acros. Solvents were obtained from Fisher Scientific or Aldrich and were used without further purification unless noted otherwise.

Preparation of trans-[2-(2-Cyclopropylmethyloxy-5-fluorophenyl)cyclopropyl]methylamine Hydrochloride (12)

Step A: trans-[2-(5-Fluorophenyl-2-hydroxy)cyclopropylmethyl]carbamic Acid tert-Butyl Ester (10). To a solution of trans-2-(5-fluorophenyl-2-hydroxy)cyclopropylmethylamine (9) (10.0 g, 55.2 mmol) and Boc$_2$O (13.2 g, 60.7 mmol) in CH$_2$Cl$_2$ (100 mL) was added triethylamine (30.8 mL, 221 mmol) at 0° C. The mixture was stirred at 0° C. for 30 min and then at rt for 30 min. To the resulting mixture were added sat. aq NaHCO$_3$. The organic layer was further washed with water (×1), dried over Na$_2$SO$_4$, and concentrated in vacuo. The residue was purified by flash chromatography using gradient elution from 0% EtOAc-hexane to 30% EtOAc-hexane to afford the title compounds as a white solid (10.5 g, 67.6% yield). $^1$H NMR (400 MHz, CDCl$_3$) δ6.79-6.74 (m, 2H), 6.62-6.59 (m, 1H), 5.04 (bs, 1H), 3.52-3.44 (m, 2H), 2.90-2.85 (m, 1H), 1.93-1.89 (m, 1H), 1.47 (s, 9H), 0.95-0.90 (m, 1H), 0.77-0.73 (m, 1H).

Step B: trans-[2-(2-Cyclopropylmethyloxy-5fluorophenyl)cyclopropylmethyl]carbamic Acid tert-Butyl Ester (11). To a solution of compound 10 (5 g, 17.8 mmol) in DMF were added K$_2$CO$_3$ (9.8 g, 71.1 mmol) and (bromomethyl)cyclopropane (6.90 mL, 71.1 mmol). After the mixture was stirred at 70° C. overnight, the organic layer was washed with brine, dried over Na$_2$SO$_4$, filtered, and concentrated. The crude product was purified by flash chromatography using gradient elution from 0% EtOAc-hexane to 20% EtOAc-hexane to afford the title compound as a colorless oil (5.8 g, 97.3% yield). $^1$H NMR (400 MHz, CDCl$_3$) δ 6.83-6.78 (m, 1 H), 6.73-6.70 (m, 1 H), 6.67-6.64 (m, 1 H), 5.31 (bs, 1H), 3.98-3.94 (m, 1 H), 3.72-3.64 (m, 2 H), 2.71-2.67 (m, 1 H), 1.90-1.85 (m, 1 H), 1.45-1.40 (m, 10 H), 1.03-0.99 (m, 2 H), 0.84-0.80 (m, 1 H), 0.69-0.65 (m, 2 H), 0.40-0.35 (m, 2 H).

Step C: The protected amine 11 (5.8 g, 17.3 mmol) was dissolved in a 2 N HCl solution in diethyl ether (43 mL, 86 mmol), and the reaction mixture was stirred at ambient temperature for 48 h. A white precipitate formed after several hours, and the mixture was stirred until the reaction was complete by TLC. The crude precipitate was filtered and purified by recrystallization from ethanol/Et$_2$O to afford the title compound as a white powder (4.3 g, 91.5% yield). HPLC purity: 12.0 min, 99.8%. $^1$H NMR (400 MHz, MeOD) δ 6.86-6.70 (m, 3 H), 3.91-3.78 (m, 2 H), 3.04 (d, J=7.2 Hz, 2 H), 2.18-2.12 (m, 1 H), 1.32-1.28 (m, 1 H), 1.16-1.02 (m, 2 H), 0.64-0.62 (m, 2 H), 0.39-0.37 (m, 2 H). $^{13}$C NMR (100 MHz, MeOD) δ 158.6 (d, 1 J CF=236.9 Hz), 155.4, 132.7 (d, 3 J CF=7.6 Hz), 114.5, 114.2, 114.2, 114.0, 114.0, 75.1, 45.2, 19.8, 18.4, 13.4, 11.4, 4.0, 3.6. MS (ESI) m/z 236.2 [MH$^+$].

Preparation of trans-[2-(2-Cyclopropylmethyloxy-5-hydroxyphenyl)cyclopropyl]methylamine Hydrochloride (18)

Step A: trans-[2-(2,5-Dihydroxyphenyl)cyclopropylmethyl]carbamic Acid tert-Butyl Ester (14). To a solution of trans-[2-(2,5-dimethoxyphenyl)cyclopropylmethyl]carbamic acid tert-butyl ester (13) (4.20 g, 13.7 mmol) in CH$_2$Cl$_2$ (30 mL) at −78° C. was added BBr$_3$ (1.0 M solution in CH$_2$Cl$_2$) (47.8 mL, 47.8 mmol) dropwise. The solution was warmed to rt, and the reaction mixture was quenched with MeOH (110 mL) and concentrated in vacuo. This process was repeated until no white fumes were observed upon addition of MeOH to give a crude product as pale yellow oils. The crude product was used without any further purification. A solution of the crude product, Boc$_2$O (3.28 g, 15.0 mmol), and triethylamine (7.62 mL, 54.7 mmol) in CH$_2$Cl$_2$ (30 mL) was stirred at rt for 30 min. To the resulting mixture were added sat. aq NaHCO$_3$, and the aqueous layer was extracted with CH$_2$Cl$_2$ (×2). The organic layer was further washed with water (×1), dried over Na$_2$SO$_4$, filtered, and concentrated in vacuo. The residue was purified by flash chromatography using gradient elution from 0% EtOAc-hexane to 30% EtOAc-hexane to afford the title compounds as a pale yellow oil (2.55 g, 66.8% yield). $^1$H NMR (400 MHz, CDCl$_3$) δ 6.73 (d, J=8.4 Hz, 1 H), 6.57 (dd, J=8.8 Hz, J=2.6 Hz, 1 H), 6.42 (d, J=2.6 Hz, 1 H), 5.01 (bs, 1 H), 4.45 (s, 1 H), 3.51-3.44 (m, 2 H), 2.92-2.85 (m, 1 H), 1.89-1.87 (m, 1 H), 1.47 (s, 9 H), 1.06-1.01 (m, 1 H), 0.92-0.90 (m, 1 H), 0.75-0.72 (m, 1 H).

Step B: trans-[2-2-Hydroxy-5-trimethylacetoxyphenyl)cyclopropylmethyl]carbamic Acid tert-Butyl Ester (15). To a stirred solution of compound 14 (1.01 g, 3.62 mmol) in anhydrous CH$_2$Cl$_2$ (10 mL) was added pivaloyl chloride (0.489 mL, 3.98 mmol) and triethylamine (0.554 mL, 3.98 mmol) at 0° C. The resulting mixture was stirred at rt for 6 h before water was added. The reaction mixture was extracted with CH$_2$Cl$_2$ (×3), and the combined organic extracts were washed with brine, dried over Na$_2$SO$_4$, filtered, and concentrated in vacuo. The residue was purified by flash chromatography using gradient elution from 0% EtOAc-hexane to 30% EtOAc-hexane to afford the title compounds as a brown oil (0.63 g, 47.9% yield). $^1$H NMR (400 MHz, CDCl$_3$) δ 7.17 (s, 1 H), 6.86 (d, J=8.4 Hz, 1 H), 6.77 (dd, J=8.8 Hz, J=2.6 Hz, 1 H), 6.59 (d, J=2.6 Hz, 1 H), 5.05 (m, 1 H), 3.52-3.45 (m, 1 H), 2.92-2.85 (m, 2 H), 1.47 (s, 9 H), 1.33 (s, 9 H), 1.08-1.03 (m, 1 H), 0.92-0.90 (m, 1 H), 0.74-0.72 (m, 1 H).

Step C: trans-[2-(2-Cyclopropylmethyloxy-5-trimethylacetoxyphenyl)cyclopropylmethyl]carbamic Acid tert-Butyl Ester (16). A solution of compound 15 (0.168 g, 0.462 mmol), (bromomethyl)cyclopropane (0.179 mL, 1.85 mmol), and K$_2$CO$_3$ (0.256 g, 1.85 mmol) in DMF (0.5 mL) was stirred at 60° C. for 24 h. The reaction mixture was diluted with EtOAc and washed with water. The aqueous layer was extracted with EtOAc (×2), and the combined organic layers were dried over Na$_2$SO$_4$, filtered, and concentrated in vacuo. The residue was purified by flash chromatography using gradient elution from 0% EtOAc-hexane to 30% EtOAc-hexane to afford the title compound as a colorless oil (0.150 g, 78% yield). $^1$H NMR (400 MHz, CDCl$_3$) δ 6.83-6.75 (m, 2 H), 6.64 (d, J=2.4 Hz, 1 H), 5.35 (bs, 1 H), 4.01-3.97 (m, 1 H), 3.74-3.67 (m, 2 H), 2.68-2.63 (m, 1 H), 1.88-1.83 (m, 1 H), 1.45-1.41 (m, 10 H), 1.33 (s, 9 H), 1.05-1.02 (m, 2 H), 0.80-0.78 (m, 1 H), 0.68-0.66 (m, S6 2 H), 0.39-0.36 (m, 2 H).

Step D: trans-[2-(2-Cyclopropylmethyloxy-5-hydroxyphenyl)cyclopropylmethyl]carbamic Acid tert-Butyl Ester (17). A solution of compound 16 (127 mg, 0.304 mmol) in MeOH (1 mL) was treated with NaOtBu (146 mg, 1.52 mmol) at 0° C. After stirring at rt for 4 h, the reaction was quenched adding sat. NH$_4$Cl (2 mL) and extracted with EtOAc. The combined organic layers were washed with brine, dried over Na$_2$SO$_4$, filtered, and concentrated in vacuo. The residue was purified by flash chromatography using gradient elution from 0% EtOAc-hexane to 30% EtOAc-hexane to afford the title compound as a thick oil (95 mg, 94% yield). $^1$H NMR (400 MHz, CDCl$_3$) δ 6.68-6.60 (m, 2 H), 6.48-6.44 (m, 2 H), 5.48 (bs, 1H), 3.94-3.90 (m, 1 H), 3.70-3.65 (m, 2 H), 2.64-2.60 (m, 1 H), 1.84-1.81 (m, 1 H), 1.45-1.39 (m, 10 H), 0.98-0.95 (m, 2 H), 0.76-0.73 (m, 1 H), 6.64-6.62 (m, 2 H), 0.35-0.34 (m, 2 H).

Step E: Prepared by the same t-Boc deprotection procedure as described for compound 12 (35 mg, 75% yield). HPLC purity: 9.0 min, 98.8%. $^1$H NMR (400 MHz, MeOD) δ 6.73 (d, J=8.8 Hz, 1 H), 6.56 (dd, J=8.8 Hz, J=3.0 Hz, 1 H), 6.41 (d, J=3.0 Hz, 1 H), 3.85-3.73 (m, 2 H), 3.05-2.97 (m, 2 H), 2.13-2.07 (m, 1 H), 1.31-1.22 (m, 2 H), 1.13-1.11 (m, 1 H), 1.02-0.99 (m, 1 H), 0.65-0.60 (m, 2 H), 0.34-0.36 (m, 2 H). $^{13}$C NMR (100 MHz, MeOD) δ 152.6, 152.5, 131.9, 114.7, 114.5, 114.3, 75.5, 45.4, 19.9, 18.4, 15.5, 13.2, 11.5, 4.0, 3.6. MS (ESI) m/z 234.2 [MH$^+$].

Preparation of (+)-trans-(S,S)-[2-(2-Cyclopropylmethyloxy-5-fluorophenyl)cyclopropyl]methylamine Hydrochloride ((+)-12)

Step A: (−)-trans-(S,S)-[2-(2-Cyclopropylmethyloxy-5-fluorophenyl)cyclopropylmethyl]carbamic Acid tert-Butyl Ester ((−)-11). Compound 11 (5 g, 18 mmol) was separated by chiral HPLC (Hexane/i PrOH, 96/4 isocratic, stack injections, flow rate of 12 mL/min, λ=280 nm) using chiralpak AD column to afford the (+)-isomer with peak 1 (2.4 g, 48% yield) and the (−)-isomer with peak 2 (2.2 g, 44% yield) as colorless solids. (+)-11: Chiral HPLC purity: 16.8 min, 99.1%. [α]D+47.2° (c 1.0, CHCl$_3$), (−)-11: Chiral HPLC purity: 13.2 min, 99.8%. [α]D −45.9° (c 1.0, CHCl$_3$).

Step B: Refer to the procedure for the synthesis of compound 12 described above with substituting compound (−)-11 (2.18 g, 6.50 mmol) for compound 11 in Step C (1.5 g, 85% yield). $^1$H NMR (400 MHz, MeOD) δ 6.86-6.70 (m, 3 H), 3.91-3.78 (m, 2 H), 3.04 (d, J=7.2 Hz, 2 H), 2.18-2.12 (m, 1 H), 1.32-1.28 (m, 1 H), 1.16-1.02 (m, 2 H), 0.64-0.62 (m, 2 H), 0.39-0.37 (m, 2 H). $^{13}$C NMR (100 MHz, MeOD) δ 158.6 (d, 1 J CF=236.9 Hz), 155.4, 132.7 (d, 3 J CF=7.6 Hz), 114.5, 114.2, 114.2, 114.0, 114.0, 75.1, 45.2, 19.8, 18.4, 13.4, 11.4, 4.0, 3.6. MS (ESI) m/z 236.2 [MH+]. [α]D+5.4° (c 1.0, MeOD).

Preparation of (+)-trans-(S,S)-[2-(2-Cyclopropylmethyloxy-5-hydroxyphenyl)cyclopropyl]methylamine Hydrochloride ((+)-18)

Step A: (−)-trans-(S,S)-[2-(2-Cyclopropylmethyloxy-5-hydroxyphenyl)cyclopropylmethyl]-carbamic Acid tert-Butyl Ester ((−)-17). Compound 17 (60 mg, 0.144 mmol) was separated by chiral HPLC (Hexane/i PrOH, 87/13 isocratic, stack injections, flow rate of 12 mL/min, λ=280 nm) using chiralpak AD column to afford the (−)-isomer with peak 1 (27.6 mg, 46% yield) and the (+)-isomer with peak 2 (28.2 mg, 47% yield) as colorless solids. (−)-17: Chiral HPLC purity: 21.9 min, 99.7%. [α]D −23.8° (c 1.0, CHCl3), (+)-17: Chiral HPLC purity: 23.9 min, 99.3%. [α]D+21.5° (c 1.0, CHCl$_3$).

Step B: Refer to the procedure for the synthesis of compound 12 described above with substituting compound (−)-17 (27.6 mg, 0.083 mmol) for compound 11 in Step C (0.018 g, 93% yield). HPLC purity: 8.0 min, 97.9%. $^1$H NMR (400 MHz, MeOD) δ 6.73 (d, J=8.8 Hz, 1 H), 6.56 (dd, J=8.8 Hz, J=3.0 Hz, 1 H), 6.41 (d, J=3.0 Hz, 1 H), 3.85-3.73 (m, 2 H), 3.05-2.97 (m, 2 H), 2.13-2.07 (m, 1 H), 1.31-1.22 (m, 2 H), 1.13-1.11 (m, 1 H), 1.02-0.99 (m, 1 H), 0.65-0.60 (m, 2 H), 0.34-0.36 (m, 2 H). $^{13}$C NMR (100 MHz, MeOD) δ 152.6, 152.5, 131.9, 114.7, 114.5, 114.3, 75.5, 45.4, 19.9, 18.4, 15.5, 13.2, 11.5, 4.0, 3.6. MS (ESI) m/z 234.2 [MH$^+$]. [α]D+18.5° (c 1.0, MeOD).

In one embodiment, the present invention relates to a method of treating an individual suffering from a disease or condition wherein agonism of 5-HT(2C) receptors provides a benefit comprising administering a therapeutically effective amount of a compound of structural formula (I) to an individual in need thereof.

The methods described herein relate to the use of a compound of structural formula (I) and an optional second therapeutic agent useful in the treatment of diseases and conditions wherein modulation of 5HT(2C) receptor activity provides a benefit. The methods of the present invention can be accomplished by administering a compound of structural formula (I) as the neat compound or as a pharmaceutical composition. Administration of a pharmaceutical composition, or a neat compound of structural formula (I), can be performed during or after the onset of the disease or condition of interest. Typically, the pharmaceutical compositions are sterile, and contain no toxic, carcinogenic, or mutagenic compounds that would cause an adverse reaction when administered.

In many embodiments, a compound of structural formula (I) is administered in conjunction with a second therapeutic agent useful in the treatment of a disease or condition wherein modulation of 5-HT(2C) receptors provides a benefit. The second therapeutic agent is different from the compound of structural formula (I). A compound of structural formula (I) and the second therapeutic agent can be administered simultaneously or sequentially. In addition, a compound of structural formula (I) and second therapeutic agent can be administered from a single composition or two separate compositions. A compound of structural formula (I) and the second therapeutic agent can be administered simultaneously or sequentially to achieve the desired effect.

The second therapeutic agent is administered in an amount to provide its desired therapeutic effect. The effective dosage range for each second therapeutic agent is known in the art, and the second therapeutic agent is administered to an individual in need thereof within such established ranges.

The present invention therefore is directed to compositions and methods of treating diseases or conditions wherein modulation of 5-HT(2C) receptors provides a benefit. The present invention also is directed to pharmaceutical compositions comprising a compound of structural formula (I) and an optional second therapeutic agent useful in the treatment of diseases and conditions wherein modulation of 5-HT(2C) receptors provides a benefit. Further provided are kits comprising a compound of structural formula (I) and, optionally, a second therapeutic agent useful in the treatment of diseases and conditions wherein modulation of 5-HT(2C) receptors provides a benefit, packaged separately or together, and an insert having instructions for using these active agents.

A compound of structural formula (I) and the second therapeutic agent can be administered together as a single-unit dose or separately as multi-unit doses, wherein the compound of structural formula (I) is administered before the second therapeutic agent or vice versa. One or more dose of the compound of structural formula (I) and/or one or more dose of the second therapeutic agent can be administered. The compounds of structural formula (I) therefore can be used in conjunction with one or more second therapeutic agent, for example, but not limited to, known drugs to treat psychiatric disorders.

Within the meaning of the present invention, the term "disease" or "condition" or "disorder" denotes disturbances and/or anomalies that as a rule are regarded as being pathological conditions or functions, and that can manifest themselves in the form of particular signs, symptoms, and/or malfunctions. As demonstrated below, a compound of structural formula (I) is a potent modulator of 5-HT(2C) receptors and can be used in treating diseases and conditions wherein modulation of 5-HT(2C) receptors provides a benefit.

Compounds of structural formula (I) therefore generally function as modulators (agonists, partial agonist, antagonists, partial antagonists as well as selective agonists) of the 5-HT (2) family of receptors. More specifically, the present compounds function as agonists of 5-HT(2) receptors. Even more specifically, the present compounds invention function as agonists or selective agonists of the 5-HT(2C) receptors. The compounds of structural formula (I) therefore can be used in the treatment of diseases, conditions, and disorders, or amelioraton of undesired symptoms, associated with the 5-HT (2C) receptor.

Diseases, conditions, disorders symptoms associated with the 5-HT(2C) receptor include among others, obesity, eating disorders, diabetes, cardiovascular disorders, sleep disorders (e.g., sleep apnea), disorders of the central nervous system, damage to the central nervous system (e.g., trauma, stroke, or spinal cord injury), gastrointestinal disorders, depression, atypical depression, bipolar disorders, anxiety disorders, obsessive-compulsive disorders, social phobias or panic, sexual dysfunction, psychoses, schizophrenia, migraine, other conditions associated with cephalic pain or other pain, raised intracranial pressure, epilepsy, personality disorders, Alzheimer's disease, age-related behavioral disorders, behavioral disorders associated with dementia, organic mental disorders, mental disorders in childhood, aggressivity, age-related memory disorders, chronic fatigue syndrome, drug and alcohol addiction, bulimia, anorexia nervosa, and premenstrual tension.

5-HT(2C) receptor-associated disorders, conditions, diseases, and symptoms that can be treated by compounds of structural formula (I) include among others: obesity, eating disorders (e.g., hyperphagia, bulimia, or anorexia nervosa), gastrointestinal disorders, malfunction of gastrointestinal motility, diabetes, sleep disorders, sleep apnea, hypertension, hypertension, hyperlipidemia, cardiovascular disease, central nervous system disorders, damage to the central nervous system associated with trauma, stroke, or spinal cord injury or complications, psychiatric disorders, obsessive-compulsive disorder, anxiety, panic disorder, schizophrenia, schizoaffective disorder, schizophreniform disorder, L-DOPA-induced psychosis, psychosis, dementia, memory deficit, intellectual deficit associated with Alzheimer's disease, bipolar disorders, adjustment disorders, depression, movement disorders, dystonia, chronic pain, Parkinson's Disease, Alzheimer's Disease, sexual dysfunction in males or females, erectile dysfunction, epilepsy, headache, and migraines. 5-HT(2C) receptor agonists are particularly useful for treatment of obesity and comorbidities thereof, including Type II diabetes, cardiovascular disease, hypertension, hyperlipidemia, stroke, osteoarthritis, sleep apnea, gall bladder disease, gout, some cancers, some infertility, and early mortality.

5-HT(2C) receptor agonists also are useful in the methods of decreasing food intake in an individual, of inducing satiety in an individual, of controlling weight gain of an individual, and in generally providing benefit to individuals in the form of weight reduction.

Additional diseases and conditions associated with the 5-HT(2C) receptor, and treatable by a present compound, are disclosed in U.S. Patent Publication No. 2008/0119477 and WO 2006/065600, each incorporated herein by reference in its entirety.

The present invention provides methods of treating disorders, diseases, conditions, and symptoms in a mammal and particularly in a human, by administering to an individual in need of treatment or prophylaxis, a therapeutically effective amount of a compound of this invention to the mammal in need thereof. The result of treatment can be partially or completely alleviating, inhibiting, preventing, ameliorating, and/or relieving the disorder, condition, or one or more symptoms thereof. Administration includes any form of administration that is known in the art to be effective for a given type of disease or disorder, is intended to encompass administration in any appropriate dosage form and further is intended to encompass administration of a compound, pharmaceutically acceptable salt, solvate, or ester thereof, alone or in a pharmaceutically acceptable carrier thereof, or administration of a prodrug derivative or analog of a compound of this invention which will form an equivalent amount of the active compound or substance within the body. An indivual in need of treatment or prophylaxsis includes those who have been diagnosed to have a given disorder or condition and to those who are suspected, for example, as a consequence of the display of certain symptoms, of having such disorders or conditions.

In one preferred embodiment, the present invention provides methods for treating the diseases and conditions disclosed above comprising administering to a subject in need thereof a therapeutically effective amount of a compound of structural formula (I).

In one embodiment, the invention provides a method for treating the diseases and conditions disclosed above comprising administering to a subject in need thereof an amount of a compound of structural formula (I), or a pharmaceutically acceptable salt thereof, sufficient to treat the condition. A composition of structural formula (I) can be used as the sole therapeutic agent, or in combination with a second treatment for the condition.

In a further embodiment, the present invention provides a method for treating a disease or condition disclosed above comprising: (a) administering to an individual in need thereof an amount of a compound of structural formula (I); and (b) administering to the individual an amount of a second therapeutic agent useful in the treatment of the disease or condition. The amounts administered are each effective to treat the disease or condition. In another embodiment, the amounts are together effective to treat the disease or condition.

In another embodiment, the invention provides a method for treating a disease or condition disclosed above, said method comprising administering to a subject in need thereof a pharmaceutical composition comprising an amount of a compound of structural formula (I) effective to treat the disease or condition.

In one embodiment, a compound of structural formula (I) or a pharmaceutically acceptable salt thereof is administered prior to the administration of the second therapeutic agent.

In another embodiment, a compound of structural formula (I) or a pharmaceutically acceptable salt thereof is administered adjunctively with the second therapeutic agent.

Suitable pharmaceutical agents that can be used in combination with the compounds of structural formula (I) include anti-obesity agents, such as apolipoprotein-B secretion/microsomal triglyceride transfer protein (apo-B/MTP) inhibitors, MCR-4 agonists, cholescystokinin-A (CCKA) agonists, serotonin and norepinephrine reuptake inhibitors (for example, sibutramine), sympathomimetic agensts, $\beta_3$ adrenergic receptor agonists, dopamine agonists (for example, bromocriptine), melanocyte-stimulating hormone receptor analogs, cannabinoid 1 receptor antagonists (for example, SR141716: N-(piperidin-1-yl)-5-(4-chlorophenyl)-1-(2,4-dichlorophenyl)-4-methyl-1H-pyrazole-3-carboxamide], melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like), and appetite suppressants (for example, bupropion). In some embodiments, the anti-obesity agents are selected from the group consisting of orlistat, sibutramine, bromocriptine, ephedrine, leptin, phentermine, and pseudoephedrine.

Other anti-obesity agents, including the agents set forth above, are well known, or will be readily apparent in light of the instant disclosure, to one of ordinary skill in the art.

It will be understood that the scope of combination-therapy of the compounds of the present invention with other anti-obesity agents, anorectic agents, appetite suppressant and related agents is not limited to those listed above, but includes in principle any combination with any pharmaceutical agent or pharmaceutical composition useful for the treatment of overweight and obese individuals.

Other suitable pharmaceutical agents, in addition to anti-obesity agents, that can be used in combination with the compounds of structural (I) include agents useful in the treatment of concomitant diseases. For example, individuals that are over weight or obese increase their risk of morbidity and mortality arising from concomitant diseases, such as, but not limited to, congestive heart failure, type II diabetes, atherosclerosis, dyslipidemia, hyperinsulinemia, hypertension, insulin resistance, hyperglycemia, retinopathy, nephropathy and neuropathy. Treatment for one or more of the diseases cited herein include the use of one or more pharmaceutical agents known in the art belonging to the classes of drugs referred to, but not limited to, the following: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists and adiponectin. In accordance to one aspect of the present invention, a compound of the present can be used in combination with a pharmaceutical agent or agents belonging to one or more of the classes of drugs cited herein.

Some embodiments of the present invention include methods of treatment of a disease, disorder, or condition as described herein comprising administering to an individual in need of such treatment a therapeutically effect amount or dose of a compound of structural formula (I) in combination with at least one pharmaceutical agent selected from the group consisting of: sulfonylureas, meglitinides, biguanides, α-glucosidase inhibitors, peroxisome proliferatorsactivated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists and adiponectin.

Suitable pharmaceutical agents that can be used in conjunction with compounds of structural formula (I) include α-glucosidase inhibitors. α-Glucosidase inhibitors belong to the class of drugs which competitively inhibit digestive enzymes such as α-amylase, maltase, α-dextrinase, sucrase, etc. in the pancreas and or small intesting. The reversible inhibition by α-glucosidase inhibitors retard, diminish or otherwise reduce blood glucose levels by delaying the digestion of starch and sugars. Some representative examples of α-glucosidase inhibitors include acarbose, N(1,3-dihydroxy-2-propyl)valiolamine (generic name; voglibose), miglitol, and α-glucosidase inhibitors known in the art.

Suitable pharmaceutical agents that can be used in conjunction with compounds of the present invention include sulfonylureas. The sulfonylureas (SU) are drugs which promote secretion of insulin from pancreatic 13 cells by transmitting signals of insulin secretion via SU receptors in the cell membranes. Examples of the sulfonylureas include glyburide, glipizide, glimepiride, and other sulfonylureas known in the art.

Suitable pharmaceutical agents that can be used in conjunction with compounds of structural formula (I) include the meglitinides. The meglitinides target postprandial hyperglycemia and show comparable efficacy to sulfonylureas in reducing $HbA_{1c}$. Examples of meglitinides include repaglinide, nateglinide, and other meglitinides known in the art.

Suitable pharmaceutical agents that can be used in conjunction with compounds of structural formula (I) include the biguanides. The biguanides represent a class of drugs that stimulate anaerobic glycolysis, increase the sensitivity to insulin in the peripheral tissues, inhibit glucose absorption from the intestine, suppress of hepatic gluconeogenesis, and inhibit fatty acid oxidation. Examples of biguanides include phenformin, metformin, buformin, and biguanides known in the art.

Suitable pharmaceutical agents that can be used in conjunction with compounds of structural formula (I) include the α-glucosidase inhibitors. The α-glucosidase inhibitors competitively inhibit digestive enzymes, such as α-amylase, maltase, α-dextrinase, sucrase, etc., in the pancreas and or small intestine. The reversible inhibition by α-glucosidase inhibitors retard, diminish or otherwise reduce blood glucose levels by delaying the digestion of starch and sugars. Examples of α-glucosidase inhibitors include acarbose, N-(1,3-dihydroxy-2-propyl)valiolamine (generic name voglibose), miglitol, and α-glucosidase inhibitors known in the art.

Suitable pharmaceutical agents that can be used in conjunction with compounds of structural formula (I) include the peroxisome proliferators-activated receptor-γ (i.e., PPAR-γ) agonists. The peroxisome proliferators-activated receptor-γ agonists represent a class of compounds that activates the nuclear receptor PPAR-γ and therefore regulate the transcription of insulin-responsive genes involved in the control of glucose production, transport and utilization. Agents in the class also facilitate the regulation of fatty acid metabolism. Examples of PPAR-γ agonists include rosiglitazone, pioglitazone, tesaglitazar, netoglitazone, GW-409544, GW-501516, and PPAR-γ agonists known in the art.

Suitable pharmaceutical agents that can be used in conjunction with compounds of structural formula (I) include the HMG-CoA reductase inhibitors. The HMG-CoA reductase inhibitors are agents also referred to as Statin compounds that belong to a class of drugs that lower blood cholesterol levels by inhibiting hydroxymethylglutalyl CoA (HMG-CoA) reductase. HMG-CoA reductase is the rate-limiting enzyme in cholesterol biosynthesis. The statins lower serum LDL concentrations by upregulating the activity of LDL receptors and are responsible for clearing LDL from the blood. Some representative examples the statin compounds include rosuvastatin, pravastatin and its sodium salt, simvastatin, lovastatin, atorvastatin, fluvastatin, cerivastatin, rosuvastatin, pitavastatin, BMS's "superstatin", and HMG-CoA reductase inhibitors known in the art.

Suitable pharmaceutical agents that can be used in conjunction with compounds of the present invention include the angiotensin converting enzyme (ACE) inhibitors. The angiotensin converting enzyme inhibitors belong to the class of drugs that partially lower blood glucose levels as well as lowering blood pressure by inhibiting angiotensin converting enzymes. Examples of the angiotensin converting enzyme inhibitors include captopril, enalapril, alacepril, delapril; ramipril, lisinopril, imidapril, benazepril, ceronapril, cilazapril, enalaprilat, fosinopril, moveltopril, perindopril, quinapril, spirapril, temocapril, trandolapril, and angiotensin converting enzyme inhibitors known in the art.

Suitable pharmaceutical agents that can be used in conjunction with compounds of the present invention include the angiotensin II receptor antagonists. Angiotensin II receptor antagonists target the angiotensin II receptor subtype 1 (i.e., AT1) and demonstrate a beneficial effect on hypertension. Examples of angiotensin II receptor antagonists include losartan (and the potassium salt form), and angiotensin II receptor antagonists known in the art.

Other treatments for one or more of the diseases cited herein include the use of pharmaceutical agents known in the art belonging to the classes of drugs referred to, but not limited to, the following: amylin agonists (for example, pramlintide), insulin secretagogues (for example, GLP-1 agonists;

exendin-4; insulinotropin (NN2211); dipeptyl peptidase inhibitors (for example, NVP-DPP-728), acyl CoA cholesterol acetyltransferase inhibitors (for example, Ezetimibe, eflucimibe, and like compounds), cholesterol absorption inhibitors (for example, ezetimibe, pamaqueside and like compounds), cholesterol ester transfer protein inhibitors (for example, CP-529414, JTT-705, CETi-1, and like compounds), microsomal triglyceride transfer protein inhibitors (for example, implitapide, and like compounds), cholesterol modulators (for example, NO-1886, and like compounds), bile acid modulators (for example, GT103-279 and like compounds), and squalene synthase inhibitors.

Squalene synthesis inhibitors belong to a class of drugs that lower blood cholesterol levels by inhibiting synthesis of squalene. Examples of the squalene synthesis inhibitors include (S)-α-[Bis [2,2-dimethyl-1-oxopropoxy)methoxy] phosphinyl]-3-phenoxybenzenebutanesulfonic acid, mono potassium salt (BMS-188494), and squalene synthesis inhibitors known in the art.

In the present method, a therapeutically effective amount of one or more compound of structural formula (I), typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms, and/or malfunctions, and other factors.

A compound of structural formula (I) can be administered by any suitable route, for example by oral, buccal, inhalation, topical, topical ophthalmic, intranasal, intrabronchial, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a compound of structural formula (I) is present in a sufficient amount to be administered in an effective amount to achieve its intended purpose. The exact formulation, route of administration, and dosage is determined by an individual physician in view of the diagnosed condition or disease. Dosage amount and interval can be adjusted individually to provide levels of a compound of structural formula (I) that is sufficient to maintain therapeutic effects.

Toxicity and therapeutic efficacy of the compounds of structural formula (I) can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds that exhibit high therapeutic indices are preferred. The data obtained from such data can be used in formulating a dosage range for use in humans. The dosage preferably lies within a range of circulating compound concentrations that include the $ED_{50}$ with little or no toxicity. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a compound of structural formula (I) required for use in therapy varies with the nature of the disease or condition being treated, the length of time that activity is desired, and the age and the condition of the patient, and ultimately is determined by the attendant physician. Dosage amounts and intervals can be adjusted individually to provide plasma levels of a compound/structural formula (I) that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a compound of structural formula (I) can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

The dosage of a composition containing a compound of structural formula (I), or a composition containing the same, can be from about 1 ng/kg to about 200 mg/kg, about 1 μg/kg to about 100 mg/kg, or about 1 mg/kg to about 50 mg/kg of body weight. The dosage of a composition may be at any dosage including, but not limited to, about 1 μg/kg, 10 μg/kg, 25 μg/kg, 50 μg/kg, 75 μg/kg, 100 μg/kg, 125 μg/kg, 150 μg/kg, 175 μg/kg, 200 μg/kg, 225 μg/kg, 250 μg/kg, 275 μg/kg, 300 μg/kg, 325 μg/kg, 350 μg/kg, 375 μg/kg, 400 μg/kg, 425 μg/kg, 450 μg/kg, 475 μg/kg, 500 μg/kg, 525 μg/kg, 550 μg/kg, 575 μg/kg, 600 μg/kg, 625 μg/kg, 650 μg/kg, 675 μg/kg, 700 μg/kg, 725 μg/kg, 750 μg/kg, 775 μg/kg, 800 μg/kg, 825 μg/kg, 850 μg/kg, 875 μg/kg, 900 μg/kg, 925 μg/kg, 950 μg/kg, 975 μg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

A compound of structural formula (I) used in a method of the present invention typically is administered in an amount of about 0.005 to about 500 milligrams per dose, about 0.05 to about 250 milligrams per dose, or about 0.5 to about 100 milligrams per dose. For example, a compound of structural formula (I) can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The compounds of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of compounds of structural formula (I).

The term "carrier" refers to a diluent, adjuvant, or excipient, with which a compound of structural formula (I) is administered. Such pharmaceutical carriers can be liquids, such as water and oils, including those of petroleum, animal, vegetable or synthetic origin, such as peanut oil, soybean oil, mineral oil, sesame oil, and the like. The carriers can be saline, gum acacia, gelatin, starch paste, talc, keratin, colloidal silica, urea, and the like. In addition, auxiliary, stabilizing, thickening, lubricating and coloring agents can be used. The pharmaceutically acceptable carriers are sterile. Water is a preferred carrier when a compound of structural formula (I) is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of a compound of structural formula (I) is administered orally, the composition typically is in the form of a tablet, capsule, powder, solution, pill, granule, tincture, emulsion, syrup, or elixir. When administered in tablet form, the composition additionally can contain a solid carrier, such as a gelatin or an adjuvant. The tablet, capsule, and powder contain about 0.01% to about 95%, and preferably from about 1% to about 50%, of a compound of structural formula (I). When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a compound of structural formula (I).

When a therapeutically effective amount of a compound of structural formula (I) is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle. A compound of structural formula (I) can be infused with other fluids over a 10-30 minute span or over several hours.

Compounds of structural formula (I) can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the compound of structural formula (I) to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A compound of structural formula (I) can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulating agents such as suspending, stabilizing, and/or dispersing agents.

Pharmaceutical compositions for parenteral administration include aqueous solutions of the active agent in water-soluble form. Additionally, suspensions of a compound of structural formula (I) can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A compound of structural formula (I) also can be formulated in rectal compositions, such as suppositories or retention enemas, e.g., containing conventional suppository bases. In addition to the formulations described previously, a compound of structural formula (I) also can be formulated as a depot preparation. Such long-acting formulations can be administered by implantation (for example, subcutaneously or intramuscularly) or by intramuscular injection. Thus, for example, the compounds of structural formula (I) can be formulated with suitable polymeric or hydrophobic materials (for example, as an emulsion in an acceptable oil) or ion exchange resins.

In particular, the compounds of structural formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The compounds of structural formula (I) also can be injected parenterally, for example, intravenously, intramuscularly, subcutaneously, or intracoronarily. For parenteral administration, the compounds of structural formula (I) are best used in the form of a sterile aqueous solution which can contain other substances, for example, salts or monosaccharides, such as mannitol or glucose, to make the solution isotonic with blood.

Compounds of structural formula (I) were prepared and assayed for an ability to modulate the activity of the 5-HT(2) family of receptors. In particular, compounds 50-53 were prepared and assayed to determine effects on the 5-HT(2) family of receptors. The results are summarized in Table 1.

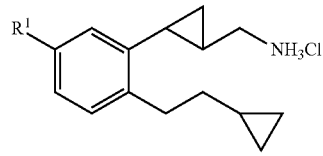

TABLE 1

| Compound No. | $R^1$ | 2A Receptor | | 2B Receptor | | 2C Receptor | |
| --- | --- | --- | --- | --- | --- | --- | --- |
| | | $ED_{50}$ | Emax | $ED_{50}$ | Emax | $ED_{50}$ | Emax |
| 50 | H | NA | | NA | | 149 | 35 |
| 50 | H | NA | | NA | | 120 | 60 |
| 51 | Br | NA | | NA | | 87 | 92 |
| 52 | Me | 13860 | 47 | 550 | 35 | 23 | 98 |
| 53 | i-Pr | 1922 | 92 | 388 | 66 | 101 | 93 |

NA = No activity

The data show that compounds 50 and 51 show no activity at 5-HT(2A) and 5-HT(2B) receptors, while modulating the 5-HT(2C) receptors.

Compounds 12 and 18, including the (+) and (−)-enantiomers, also were tested for their effect on the 5-HT(2) family of receptors. The functional activity of these compounds was determined by measuring Gαq-mediated intracellular calcium mobilization in HEK-293 cells stably expressing the human 5-HT(2A), human 5-HT(2B), and human 5-HT(2C) (INI) receptors (18). The results are summarized in Table 2.

In the functional assays, racemic compound 12 was found not to activate either the 5-HT(2A) or 5-HT(2B) receptors, and to have an $EC_{50}$ of 254 nM at the 5-HT(2C) receptor. The more active enantiomer (+)-12 also showed a selectivity profile in these in vitro functional assays. In contrast, the less active isomer (−)-12 had an $EC_{50}$ of about 2.4 µM in the 5-HT(2C) assay.

For comparison purposes, the 5-HT(2C) ligand Lorcaserin (2), which is in Phase III clinical trials for obesity, was tested. Compound 2 has a low nM potency at the 5-HT(2C) receptor. However, it is also fairly active at the 5-HT(2B) subtype, with an $EC_{50}$ of 124 nM and an $E_{max}$ of 92%. Accordingly, valvulopathy may be induced by compound 2. Three other known 5-HT(2C) agonists, Vabicaserin (3) and the Way compounds (4) and (5) along with 5-HT also were included in the assays for reference purposes. The pharmacological profile shown by compound WAY 629 (5) is similar to that shown by compound (+)-12.

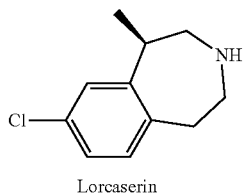

Lorcaserin (2)

Vabicaserin (3)

WAY 161503 (4)

WAY 629 (5)

In order to further characterize the pharmacology of both (+)-12 and (+)-18, which show minimal 5-HT(2B) activation, the compounds were tested for their ability to function as 5-HT(2B) antagonists. Compounds (+)-12 and (+)-18 were found to shift the concentration curve of 5-HT in calcium flux experiments rightwards without depressing the maximal 5-HT response, indicating fast binding kinetics. Schild analyses yielded pA2 (±SEM) values of 5.50±0.06, 5.79±0.07, and 5.92±0.02, respectively (n=3). These results show that the tested compounds act as moderate potency, full antagonists at the 5-HT(2B) receptor.

TABLE 2

Functional Activity and Selectivity of Compound 12 and its Enantiomers (+)-12 and (−)-12 at Human 5-HT$_{2A}$, 5-HT$_{2B}$, and 5-HT$_{2C}$ Receptors in Calcium Flux Assays Using Stably Transfected HEK-293 Cells

| Compd$^a$ | 5-HT$_{2A}$ | | | 5-HT$_{2B}$ | | | 5-HT$_{2C}$ | | | Selectivity | | | $E_{max}$ | |
| --- | --- | --- | --- | --- | --- | --- | --- | --- | --- | --- | --- | --- | --- | --- |
| | EC50 ± SEM (nM) | % Max ± SEM$^b$ | n$^c$ | EC50 ± SEM (nM) | % Max ± SEM$^b$ | n$^c$ | EC50 ± SEM (nM) | % Max ± SEM$^b$ | n$^c$ | 2A/2C | 2B/2C | 2C/2A | 2C/2B |
| 5-HT | 6.9 ± 0.42 | 100% | 15 | 0.73 ± 0.02 | 100% ± 0.0% | 16 | 0.11 ± 0.01 | 100% ± 0.0% | 16 | 63 | 6.7 | 1.0 | 1.0 |
| 12 | 761 ± 160 | 11% ± 1.9% | 3 | NA | 2% ± 0.9% | 3 | 9.9 ± 1.7 | 68% ± 4.5% | 3 | 77 | — | 6.2 | 38 |
| 18 | NA | 7% ± 1.8% | 3 | NA | 6% ± 0.6% | 3 | 19 ± 3.5 | 68% ± 5.2% | 3 | — | — | 9.4 | 12 |
| 2 (Lorcaserin) | 264 ± 31 | 24% ± 0.9% | 6 | 85 ± 7.0 | 93% ± 1.2% | 6 | 2.1 ± 0.29 | 99% ± 1.0% | 7 | 123 | 40 | 4.2 | 1.1 |
| 3 (Vabicaserin) | NA | 2% ± 0.1% | 6 | NA | 5% ± 1.0% | 6 | 6.0 ± 1.0 | 95% ± 0.8% | 7 | — | — | 56 | 19 |
| 4 (WAY-161503) | 76 ± 9.1 | 80% ± 1.0% | 3 | 15 ± 1.6 | 92% ± 1.3% | 3 | 1.1 ± 0.16 | 97% ± 1.6% | 4 | 70 | 14 | 1.2 | 1.1 |
| 5 (WAY 629) | NA | 1% ± 0.2% | 6 | NA | 6% ± 1.3% | 6 | 286 ± 40 | 80% ± 1.1% | 7 | — | — | 140 | 13 |
| 5-HT | 6.1 ± 0.38 | 100% ± 0.0% | 9 | 0.76 ± 0.08 | 100% ± 0.0% | 9 | 0.10 ± 0.00 | 100% ± 0.0% | 9 | 62 | 7.7 | 1.0 | 1.0 |
| (+)-12 | 894 ± 91 | 29% ± 1.6% | 3 | 289 ± 34 | 21% ± 4.9% | 3 | 21 ± 2.2 | 71% ± 4.4% | 3 | 42 | 14 | 2.5 | 3.4 |
| (−)-12 | NA | 0% ± 0.0% | 3 | NA | 4% ± 2.7% | 3 | 918 ± 83 | 35% ± 2.4% | 3 | — | — | ≫ | 8.0 |

TABLE 2-continued

Functional Activity and Selectivity of Compound 12 and its Enantiomers (+)-12 and (−)-12 at Human 5-HT$_{2A}$, 5-HT$_{2B}$, and 5-HT$_{2C}$ Receptors in Calcium Flux Assays Using Stably Transfected HEK-293 Cells

| | 5-HT$_{2A}$ | | | 5-HT$_{2B}$ | | | 5-HT$_{2C}$ | | | Selectivity | | E$_{max}$ | |
|---|---|---|---|---|---|---|---|---|---|---|---|---|---|
| Compd[a] | EC50 ± SEM (nM) | % Max ± SEM[b] | n[c] | EC50 ± SEM (nM) | % Max ± SEM[b] | n[c] | EC50 ± SEM (nM) | % Max ± SEM[b] | n[c] | 2A/2C | 2B/2C | 2C/2A | 2C/2B |
| (+)-18 | 372 ± 131 | 18% ± 3.0% | 3 | NA | 6% ± 2.8% | 3 | 9.3 ± 0.05 | 70% ± 5.4% | 3 | 40 | — | 3.9 | 11 |
| (−)-18 | NA | 3% ± 0.6% | 3 | NA | 0% ± 0.5% | 3 | 361 ± 21 | 51% ± 2.4% | 3 | — | — | 19 | >> |
| 2 (Lorcaserin) | 136 ± 24 | 31% ± 0.5% | 3 | 50 ± 10 | 86% ± 2.3% | 3 | 1.7 ± 0.09 | 94% ± 0.8% | 3 | 79 | 29 | 3.0 | 1.1 |
| 3 (Vabicaserin) | NA | 7% ± 0.1% | 3 | 47 ± 6.4 | 15% ± 3.3% | 3 | 8.0 ± 1.6 | 88% ± 1.8% | 3 | — | 5.8 | 12 | 5.9 |
| 4 (WAY-161503) | 61 ± 8.3 | 79% ± 4.5% | 3 | 16 ± 3.2 | 86% ± 4.7% | 3 | 1.5 ± 0.18 | 94% ± 3.6% | 3 | 40 | 11 | 1.2 | 1.1 |
| 5 (WAY 629) | NA | 7% ± 2.0% | 3 | >5 μM | 17% ± 2.7% | 3 | 451 ± 52 | 82% ± 3.5% | 3 | — | — | 12 | 4.7 |

[a]Tested in two independent screening campaigns using different cell lines/passages; direct comparisons of the potencies and efficacies are only valid within the bounds of each particular table section.
[b]Percent of maximal activation by 5-HT; activation at 10 μM for compounds without EC$_{50}$ value.
[c]n: Number of concentration curves from ≥2 (typically ≥3) independent experiments.
NA: E$_{max}$ ≤ 12%. In contrast to binding affinities, the potencies in functional assays can vary strongly depending on cell type, receptor expression level, and passage number On the basis of their in vitro pharmacology, enantiomers (+)-12 and (+)-18 were subjected to further in vivo studies. Specifically, the ability of these compounds to normalize disrupted prepulse inhibition (PPI) in PCP treated animals was tested. PPI is a neuropsychiatric animal model in which a weaker prestimulus, the 'prepulse', is able to inhibit the reaction of an animal to a subsequent much stronger, startling stimulus, or 'pulse'. Typically, the stimulus that is used in such studies is a sound (units in decibells or dB), but other stimuli such as touch, light, or a puff of air can be used. The reduction in the strength of the startle response is indicative of the ability of the nervous system to temporarily adapt to a strong sensory stimulus when an earlier, weaker signal is given to warn the organism. While the extent to which the organism is able to adjust to the stimulus affects a host of physiological systems, it is generally convenient to measure any changes in the muscular reactions, in order to gauge the effects of a drug on PPI. It is well known that schizophrenics often show a disruption of the PPI response as a consequence of so-called sensory flooding, and thus their inability to filter out unimportant information. (Swerdlow et al., Arch Gen Psychiatry. 1994; 51(2):139-154).

The ability of the present 5-HT(2C) ligands to normalize the effects of phencyclidine (PCP, an NMDA receptor antagonist)-induced disruption of PPI in mice was tested. This PCP model is a well accepted model of atypical antipsychotic activity (19, 20) and has been used previously to characterize the antipsychotic activity of 5-HT(2C) agonists (21). The ability of compounds (+)-12 and (+)-18, as well as vabicaserin (3) as the reference compound, to normalize PCP (6 mg/kg)-disrupted PPI was tested. It was found that both (+)-12 and (+) 18 were able to normalize PCP-disrupted PPI at doses of 10 mg/kg and are comparable in activity to vabicaserin. At the 5 mg/kg dose level, (+)-12 and vabicaserin are still effective.

Cytochrome P-450 screening, metabolic stability studies, and hERG assays also were performed on (+)-compound 12. The data are summarized in Tables 3-5. In the recombinant CYP inhibition test, compound (+)-12 showed relatively low inhibition against CYP2C9 (19.55%), CYP2D6 (26.97%), and CYP3A4 (21.68% and 25.13% using midazolam and testosterone as the substrates, respectively) at 10 μM. Furthermore, compound (+)-12 had an acceptable microsomal stability compared with the control drug, verapamil (Table 4) and showed no activity in the hERG assay at concentrations of 5 and 10 μM.

TABLE 3

CYPs Inhibition Profile of Compounds (+)-12

| CYP | Substrates | Test Inhibitors | % Inhibition at 10 μM |
|---|---|---|---|
| 2C9 | tolbutamide | sulfaphenazole | 94.65 |
| | | (+)-12 | 19.55 |
| 2D6 | dextromethorphan | quinidine | 98.66 |
| | | (+)-12 | 26.97 |
| 3A4 | midazolam | ketoconazole | 99.76 |
| | | (+)-12 | 21.68 |
| | testosterone | ketoconazole | 99.71 |
| | | (+)-12 | 25.13 |

TABLE 4

Drug Metabolism of Compounds (+)−12

| | Microsomal atability (% remaining)[a] | |
|---|---|---|
| Compd | human | rat |
| Verapamil | 39.61 | — |
| (+)−12 | 90.50 | 66.03 |

[a]Rat and human microsomal stabilities were determined.

Biological Assays Protocols

Calcium Flux Assays. Calcium flux assays were performed essentially as described earlier (N. H. Jensen et al., Neuropsychopharmacology. (2008) 33, 2303-2312.) HEK 293 cells stably expressing the human 5-HT(2A), 5-HT(2B), or 5-HT(2C)$_{(INI)}$ receptor were seeded and incubated for 20 h in serum-free DMEM containing 50 U/mL penicilin and 50 μg/mL streptomycin sulfate in tissue culture-treated black clear-bottom 384-well plates (Greiner, Germany); plates were coated with 20 μL/well of 50 mg/L poly-L-lysine (Sigma, P-1524) in PBS. The cells were preincubated for 75 min at 37° C. in a humidified incubator with 20 µL of reconstituted fura-4 based calcium dye (Calcium Plus Assay Kit, Molecular Devices) in assay buffer (Hanks' balanced salt solution containing calcium and magnesium (Invitrogen, 14065-056), 50 mM HEPES, 2.5 mM probenecid, 100 mg/L ascorbic acid, pH 7.4). The plates were allowed to cool to rt over 10 min and were transferred to a FLIPR Tetra fluorescence image plate reader (Molecular Devices). The test compounds in 15 µL assay buffer were automatically added and fluorescence (excitation: 470-495 nm, emission: 515-575 nm) was measured every second for 3 min. The baseline was averaged from ten data points immediately before the additions and results were exported as the maximal response over baseline during 60 s after addition. Compounds were measured at seven concentrations from 10 µM to 10 µM in triplicate. $EC_{50}$ values and $E_{max}$ values were obtained from non-linear curve fitting against a sigmoidal dose-response model using Prism (Graphpad).

Prepulse Inhibition Animal Study. Pre-pulse inhibition (PPI) testing and analysis was performed as described previously (A. I. Abbas, et al. *J Neurosci* (2009), 29, 7124-36.) Adult male and female C57BL/6J mice (Jackson Labs, Bar Harbor, Me.) ages 8 to 12 weeks were used in all experiments. Mice were pre-administered vehicle (0.9% Saline; 10 ml/kg, i.p.) or increasing doses of (+)-12, (+)-18, or vabicaserin (3) and returned to their home cage. 30 minutes later, animals were administered phencyclindine (6 mg/kg, i.p.) and immediately placement into the PPI apparatus (SR-Lab Startle Response System, San Diego Instruments). After 5 min acclimation to 62-dB white-noise, animals were administered 74 acoustic test trials, beginning and ending with 5 trials each of startle-only stimuli (40 msec 120-dB white-noise burst). The remaining 64 trials were randomized between the following trial types: 8 startle-only trails, 8 trials without any stimuli (null trials), 16 trials with prepulse stimuli (4, 8, 12, and 16 dB above the 62-dB background, 4 of each intensity, 20 msec in length) that were not paired with startle stimuli (prepulse-only trials), and 32 trials of prepulse stimuli (4, 8, 12, and 16 dB above the 62-dB background, 8 at each intensity) paired with the 120 dB startle stimulus given 100 msec following the onset of the prepulse stimulus. Trials were separated by a variable interval (8-15 sec) and total test-time lasted 26-30 min for each animal. The formula used to calculate percentage PPI was: 100-((startle after prepulse/startle without prepulse)×100). The data were analyzed with SR LAB programs and are presented as means±standard error of the mean. A repeated measures ANOVA (using Graphpad Prism 5.0) was used to examine the effects of test compounds on prepulse-dependent PPI, with prepulse intensity (4, 8, 12, and 16 dB) as the within subjects effect, and compound and dose as the between subjects effects (dose nested within compound). Differences between treatment groups were determined with Bonferroni corrected pair-wise comparisons. In all cases, $p<0.05$ was considered statistically significant.

Inhibition of CYP Isozymes. For each of the inhibition assays the following was used: $MgCl_2$ (20 µL, 50 mM solution), phosphate buffer (100 µL, 100 mM solution), water (38 µL), recombinant enzyme (20 µL, 200 µM solution), and 1 µL of one of the following substrates: tolbutamide (40 mM, for CYP2C9), dextrometorphane (2 mM, for CYP2D6), or midazolam (1 mM, for CYP3A4), and testosterone (10 mM, for CYP3A4). The final concentration of test compound is 10 µM. The mixture was pre-heated to 37° C. for two minutes after which the reaction was initiated by the addition of NADPH (20 µL, 10 mM). The reaction was heated at 37° C. for 5 (for CYP3A4) or 20 minutes (CYP 2D9 and CYP2D6) and terminated by the addition of MeCN (0.6 mL). Samples were centrifuged (16000 rpm, 10 min) and 200 µL aliquots were taken for LC-MS-MS analysis. Separation of the sample components was performed on a Waters ACQUITY UPLC C18 (2.1 mm×50 mm) column, using mobile phase mixtures between 0.1% formic acid in MeCN and 0.1% formic acid in water (elution rate 0.5 mL/min, column temperature 25° C.). The following instrument settings were used: Collision temperature 500° C., ionspray voltage +5500 V; for CYP2C9 (hydroxytolbutamied determined) Q1 287.2, Q3 188.1, DP 86 V, EP 8 V, CE 18 V, CXP 11 V; for CYP 2D6 (dextrophan determined) Q1 259.2, Q3 158.2, DP 84 V, EP 9 V, CE 52 V, CXP 8 V; for CYP3A4 (1-Hydroxymidazolam determined) Q1 343.2, Q3 325.0, DP 100 V, EP 10 V, CE 29 V, CXP 21 V and (6-β-Hydroxytestosterone) Q1 305.2, Q3 269.1, DP 70 V, EP 8 V, CE 22 V, CXP 16V.

Stability in Liver Microsomes. For each sample to be investigated, the following was mixed: microsomes (50 µL, 0.5 mg/mL), $MgCl_2$ solution (50 µL, 50 mM), phosphate buffer (250 µL, 100 mM), water (95 µL), test compound (+)-12 (5 µL, 200 µM). Verapamil was tested as a positive control. The reaction was performed at 37° C. and initiated by the addition of NADPH (50 µL, 10 mM) or, for the negative control, by the addition of water (50 µL). Aliquots of 50 µL were taken form the solution after 0, 15, 30, 45, and 60 minutes and the reaction stopped by the addition of 150 µL cold methanol to the aliquot. The samples were centrifuged (16000 rpm, 10 min). 100 µL supernatant was used for LC-MS-MS investigation. All incubations were performed in duplicate. Separation of the sample components was performed on a Waters ACQUITY UPLC C18 (2.1 mm×50 mm) column, using mobile phase mixtures between 0.1% formic acid in MeCN and 0.1% formic acid in water (elution rate 0.5 mL/min, column temperature 25° C.). The following instrument settings were used: Collision temperature 500° C., ionspray voltage +5500 V. The in vitro half-life was calculated as in vitro $t_{1/2}=-(0.693/k)$ where k is the slope determined by linear regression of the peak-area of the parent drug vs. incubation time curve. The in vitro intrinsic clearance (in vitro $CL_{int}$) was calculated according to: in vitro $CL_{int}=(0.693/t_{1/2})\times$(volume of incubation (µL)/amount of proteins (mg)).

hERG Assays. Compounds were screened for hERG inhibition at 1 µM and 10 µM using HEK-293 cells stably expressing the human hERG channel with the FluxOR thallium assay kit (Invitrogen) using a FLIPR Tetra fluorescence image plate reader (Molecular Devices). Cisapride at 1 µM and 10 µM was used as the reference standard ($IC_{50}$=490 nM). Compounds with >25% inhibition were validated using a PatchXpress 7000A automated parallel planar patch-clamp system at 32 nM-32 µM. (H. Zeng et al., *Assay Drug Dev Technol*. (2008), 6, 235-41).

Prior 5-HT(2C) agonists possessed properties that hindered their development as therapeutic agents. In accordance with an important feature of the present invention, compounds of structural formula (I) were synthesized and evaluated as inhibitors for agonists for 5-HT(2C) antagonist. The compounds of structural formula (I) are potent agonists of 5-HT(2C) receptors and are inert with respect to 5-HT(2B) and 5-HT(2A) receptors. In some embodiments, a compound of structural formula (I) is a 5-HT(2B) receptor antagonist.

References
1. J. M. Chou-Green et al., *Physiol Behay*. (2003) 78, 641-9.
2. B. A. Rocha et al., *J Neurosci* (2002) 22, 10039-45.
3. L. H. Tecott et al., *Nature*. (1995) 374, 542-6.
4. M. J. Millan et al., *Eur J. Pharmacol*. (1997), 325, 9-12.
5. D. E. Nichols et al., *Pharmacol Ther*. (2004) 101, 131-81.
6. R. B. Rothman et al., *Circulation*. (2000) 102, 2836-41.

7. B. L. Roth et al., *N Engl J. Med.* (2007) 356, 6-9.
8. J. Dunlop et al., *CNS Drug Rev.* (2006) 12, 167-77.
9. S. Burbassi et al., *Psychopharmacology (Berl).* (2008) 196, 15-27.
10. K. J. Miller, *Mol Interv.* (2005) 5, 282-91.
11. W. K. Kroeze et al., *Curr Top Med. Chem.* (2002) 2, 507-28.
12. M. Berger et al., *Annual Review of Medicine.* (2009) 60, 355-366.
13. D. A. Wacker et al., *Curr Opin Drug Discov Devel.* (2008) 11, 438-45.
14. R. G. Booth et al., *Eur J. Pharmacol.* (2009) 615, 1-9.
15. S. J. Cho et al., *J Med. Chem.* (2009) 52, 1885-902.
16. W. Wolfson, *Chem Biol.* (2008) 15, 1139-40.
17. Q. W. Yao, *Angewandte Chemie-International Edition.* (2000) 39, 3896-+.
18. N. H. Jensen et al., *Neuropsychopharmacology* (2008) 33, 2303-2312.
19. M. A. Geyer et al., *Progress in Neuro-Psychopharmacology and Biological Psychiatry.* (2003) 27, 1071-9.
20. M. A. Geyer et al., *Psychopharmacology.* (2001) 156, 117-54.
21. K. L. Marquis et al., *J Pharmacol Exp Ther.* (2007) 320, 486-96.
22. J. Dunlop et al., *J Pharmacol Exp Ther.* (2005) 313, 862-9.

What is claimed is:

1. A composition comprising (a) compound having a structural formula:

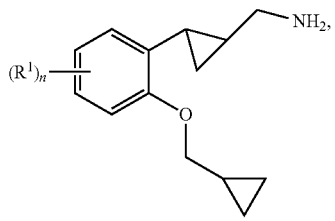

wherein $R^1$, independently, is selected from the group consisting of $C_{1-6}$alkyl, hydroxy$C_{1-6}$alkyl, halo$C_{1-6}$alkyl, $C_{1-6}$alkenyl, —$CF_3$, —$OCF_3$, $C_{1-6}$heteroalkyl, —$OR^a$, —$SR^a$, halo, —$NO_2$, —CN, —NC, —C(=O)$R^a$, —C(=C)O$R^a$, —N($R^a$)($R^b$), —C(=O)N($R^a$)($R^b$), —$SO_2$N($R^a$)($R^b$), —$NR^c$C(=O)$R^a$, —N=C($R^a$)($R^b$), —$NR^c$C(=O)O$R^a$, —$SO_2R^a$, —$SO_3R^a$, —P(O)(O$R^a$), —P(=O)(O$R^a$)(O$R^b$), and —NH—P(=O)(O$R^a$)(O$R^b$);

$R^a$ and $R^b$, independently, are selected from the group consisting of H, $C_{1-6}$alkyl, aryl, heteroaryl, cycloalkyl, and heterocycloalkyl;

$R^c$ is H or $C_{1-6}$alkyl;

and n is an integer 0, 1, 2, 3, or 4;

or a pharmaceutically acceptable salt or hydrate thereof, and (b) an excipient and/or pharmaceutically acceptable carrier.

2. A method of treating a disease or condition wherein modulation of 5-HT(2C) receptors provides a benefit comprising administering a therapeutically effective amount of a compound having a structural formula:

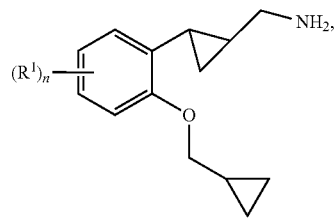

wherein $R^1$, independently, is selected from the group consisting of $C_{1-6}$alkyl, hydroxy$C_{1-6}$alkyl, halo$C_{1-6}$alkyl, $C_{1-6}$alkenyl, —$CF_3$, —$OCF_3$, $C_{1-6}$heteroalkyl, —$OR^a$, —$SR^a$, halo, —$NO_2$, —CN, —NC, —C(=O)$R^a$, —C(=C)O$R^a$, —N($R^a$)($R^b$), —C(=O)N($R^a$)($R^b$), —$SO_2$N($R^a$)($R^b$), —$NR^c$C(=O)$R^a$, —N=C($R^a$)($R^b$), —$NR^c$C(=O)=O)OR$^a$, —$SO_2R^a$, —$SO_3R^a$, —P(O)(O$R^a$), —P(=O)(O$R^a$)(O$R^b$), and —NH—P(=O)(O$R^a$)(O$R^b$);

$R^a$ and $R^b$, independently, are selected from the group consisting of H, $C_{1-6}$alkyl, aryl, heteroaryl, cycloalkyl, and heterocycloalkyl;

$R^c$ is H or $C_{1-6}$alkyl;

and n is an integer 0, 1, 2, 3, or 4;

or a pharmaceutically acceptable salt or hydrate thereof to an individual in need thereof, wherein the disease or condition is selected from the group consisting of diabetes, sleep apnea, trauma, stroke, spinal cord injury, clinical depression, bipolar disorder, schizophrenia, chronic fatigue syndrome, bulimia, anorexia nervosa, premenstrual tension, hyperphagia, hypertension, hyperlipidemia, obsessive compulsive disorder, panic disorder, psychosis, an adjustment disorder, a movement disorder, a cognition disorder, dementia, dystonia, chronic pain, Parkinson's Disease, erectile dysfunction, epilepsy, obesity, Type 2 diabetes, osteoarthritis, dyslipidemia, diabetes insipidus, metabolic syndrome, a gastrointestinal disorder, a cardiovascular disease, memory deficit, mild cognitive impairment, an intellectual deficit associated with Alzheimer's disease, Huntington's Disease, dyskinesia, migraine, epilepsy, and abuse or addiction to alcohol and drugs.

3. The method of claim 2 wherein the 5-HT(2C) receptors are activated.

4. The method of claim 2 wherein the disease or condition is selected from the group consisting of a panic disorder, schizophrenia, psychosis, an adjustment disorder, dystonia, clinical depression, bipolar disorder, an addictive behavior, obsessive compulsive disorder, a movement disorder, or a cognition disorder.

5. The method of claim 2 wherein the disease or condition is a metabolic or eating disorder selected from the group consisting of dyslipidemia, Type 2 diabetes, diabetes insipidus, metabolic syndrome, and obesity.

6. The method of claim 2 wherein the disease or condition is a gastrointestinal disorder, sleep apnea, hypertension, hyperlipidemia, a cardiovascular disease, dementia, memory deficit, mild cognitive impairment, Parkinson's Disease, an intellectual deficit associated with Alzheimer's disease, Huntington's Disease, dyskinesia, chronic pain, migraine, epilepsy, abuse or addiction to alcohol and drugs, or sexual dysfunction.

7. A method for controlling weight gain of an individual comprising administering to the individual suffering from weight control a therapeutically effective amount of a compound having a structural formula:

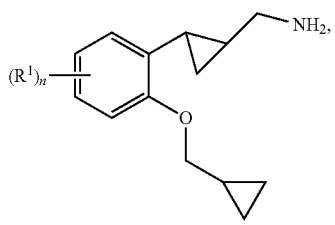

wherein R[1], independently, is selected from the group consisting of $C_{1-6}$alkyl, hydroxy$C_{1-6}$alkyl, halo$C_{1-6}$alkyl, $C_{1-6}$alkenyl, —$CF_3$, —$OCF_3$, $C_{1-6}$heteroalkyl, —$OR^a$, —$SR^a$, halo, —$NO_2$, —CN, —NC, —C(=O)$R^a$, —C(=C)$OR^a$, —N($R^a$)($R^b$), —C(=O)N($R^a$)($R^b$), —$SO_2$N($R^a$)($R^b$), —$NR^c$C(=O)$R^a$, —N=C($R^a$)($R^b$), —$NR^c$C(=O)$OR^a$, —$SO_2R^a$, —$SO_3R^a$, —P(O)($OR^a$), —P(=O)($OR^a$)($OR^b$), and —NH—P(=O)($OR^a$)($OR^b$);

$R^a$ and $R^b$, independently, are selected from the group consisting of H, $C_{1-6}$alkyl, aryl, heteroaryl, cycloalkyl, and heterocycloalkyl;

$R^c$ is H or $C_{1-6}$alkyl;

and n is an integer 0, 1, 2, 3, or 4;

or a pharmaceutically acceptable salt or hydrate thereof to an individual in need thereof.

\* \* \* \* \*